(12) United States Patent
Widdison

(10) Patent No.: US 6,913,748 B2
(45) Date of Patent: Jul. 5, 2005

(54) CROSS-LINKERS WITH HIGH REACTIVITY AND SOLUBILITY AND THEIR USE IN THE PREPARATION OF CONJUGATES FOR TARGETED DELIVERY OF SMALL MOLECULE DRUGS

(75) Inventor: Wayne Charles Widdison, Somerville, MA (US)

(73) Assignee: Immunogen, Inc., Cambridge, MA (US)

( * ) Notice: Subject to any disclaimer, the term of this patent is extended or adjusted under 35 U.S.C. 154(b) by 0 days.

(21) Appl. No.: 10/633,616

(22) Filed: Aug. 5, 2003

(65) Prior Publication Data

US 2004/0039176 A1 Feb. 26, 2004

Related U.S. Application Data

(60) Provisional application No. 60/403,652, filed on Aug. 16, 2002.

(51) Int. Cl.[7] ..................... A61K 39/395; C07D 401/00
(52) U.S. Cl. ................................ 424/178.1; 530/391.1; 540/456; 540/462; 546/278.4; 546/278.7
(58) Field of Search ................................ 540/456, 462; 546/278.7, 278.4; 424/178.1; 530/391.1

(56) References Cited

U.S. PATENT DOCUMENTS 4,563,304 A * 1/1986 Carlsson et al. ............ 530/363
6,436,931 B1 * 8/2002 Chari et al. ............... 514/232.5
6,441,162 B2 * 8/2002 Yasui et al. ................. 540/227
6,441,163 B1 * 8/2002 Chari et al. ................. 540/458
6,716,821 B2 * 4/2004 Zhao et al. .................... 514/34
2004/0235840 A1 * 11/2004 Chari et al. ............... 514/229.5

OTHER PUBLICATIONS

Yokoyama et al, Makromol. Chem, 190, 2041–2054 (1989).*

Yokoyama et al. "Molecular design for missile drug: Synthesis of adriamycin conjugated with immunoglobulin G using poly(ethylene glycol–block–(aspartic acid) as intermediate carrier." Makromol. Chem. 1989, vol. 190 pp. 2041–2054, see p. 2047, and p. 2050.

* cited by examiner

*Primary Examiner*—Christopher R. Tate
*Assistant Examiner*—Edward Ward
(74) *Attorney, Agent, or Firm*—Sughrue Mion, PLLC

(57) ABSTRACT

Disclosed is a method of making conjugates of cell binding agents and small molecule drugs comprising reacting a cell binding agent with a bifunctional cross-linking moiety to thereby provide the cell binding agent with a reactive disulfide group and then reacting the modified cell binding agent with a small molecule drug comprising a free thiol group. Bifunctional cross-linking moieties are also disclosed.

34 Claims, 8 Drawing Sheets

| X | Y | Z |
|---|---|---|
| H | H | H (Compound 3a) |
| NO$_2$ | H | H (Compound 3b) |
| NO$_2$ | H | SO$_3^-$M$^+$ (Compound 3c) |
| H | NO$_2$ | H |
| H | NO$_2$ | SO$_3^-$M$^+$ |
| NO$_2$ | NO$_2$ | H |
| NO$_2$ | NO$_2$ | SO$_3^-$M$^+$ |

M = Na, K etc

| X | Y | Z |
|---|---|---|
| $NO_2$ | H | H (Compound 4a) |
| $NO_2$ | H | $SO_3^-M^+$ (Compound 4b) |
| H | $NO_2$ | H |
| H | $NO_2$ | $SO_3^-M^+$ |
| $NO_2$ | $NO_2$ | H |
| $NO_2$ | $NO_2$ | $SO_3^-M^+$ |
| H | H | H |
| $CONMe_2$ | H | H |
| $CONMe_2$ | H | $SO_3^-M^+$ |
| H | $CONMe_2$ | H |
| H | $CONMe_2$ | $SO_3^-M^+$ |
| $CONMe_2$ | $CONMe_2$ | H |
| $CONMe_2$ | $CONMe_2$ | $SO_3^-M^+$ |

M = Na, K etc

| X | Y | Z |
|---|---|---|
| CONMe$_2$ | H | H |
| CONMe$_2$ | H | SO$_3^-$M$^+$ |
| CONMe$_2$ | CONMe$_2$ | H |
| CONMe$_2$ | CONMe$_2$ | SO$_3^-$M$^+$ |

M = Na, K etc

| X | Y | Z |
|---|---|---|
| NO$_2$ | H | H |
| NO$_2$ | H | SO$_3^-$M$^+$ |
| NO$_2$ | NO$_2$ | H |
| NO$_2$ | NO$_2$ | SO$_3^-$M$^+$ |

M = Na, K etc

Figure 7. Comparison of SSNPP and SPP for efficiency of conjugation with increasing drug equivalents in the conjugation reaction.
a) Drug per antibody ratio; b) % efficiency of conjugation based on linker to antibody ratios of 4.2 for SSNPP and 5.6 for SPP.
A
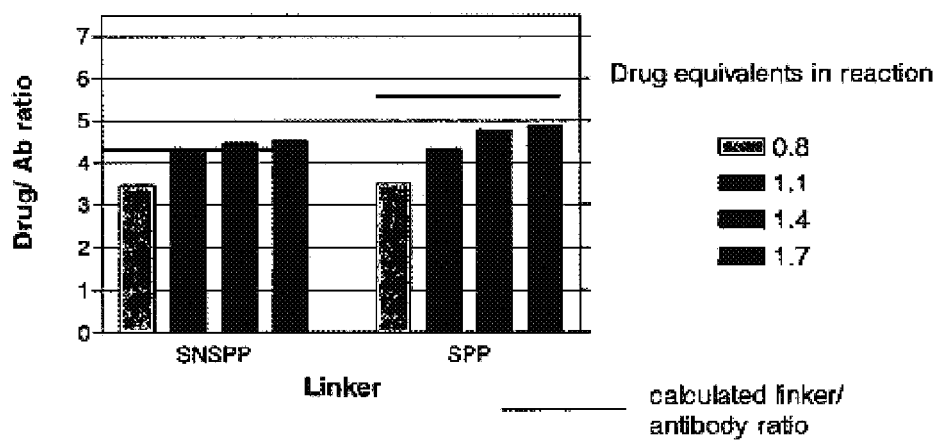
B
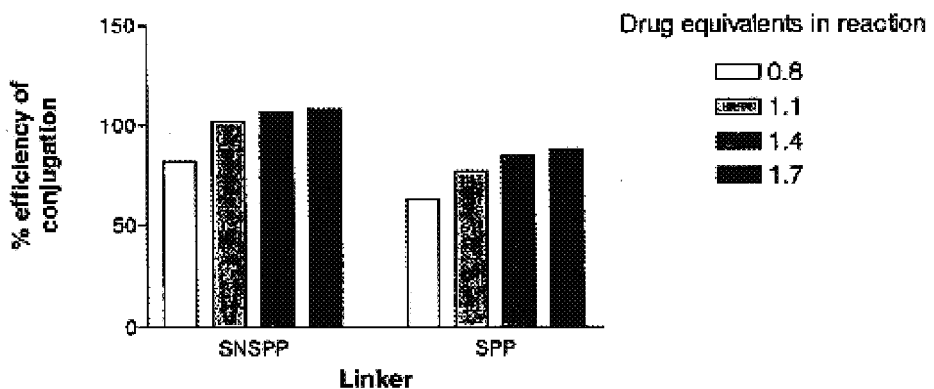

Figure 8. Time course for thiol exchange with SSNPP and SPP linker at pH 7.4 Conjugation was conducted at pH 7.4 using a 1.1-fold molar excess of DM1 per linker.
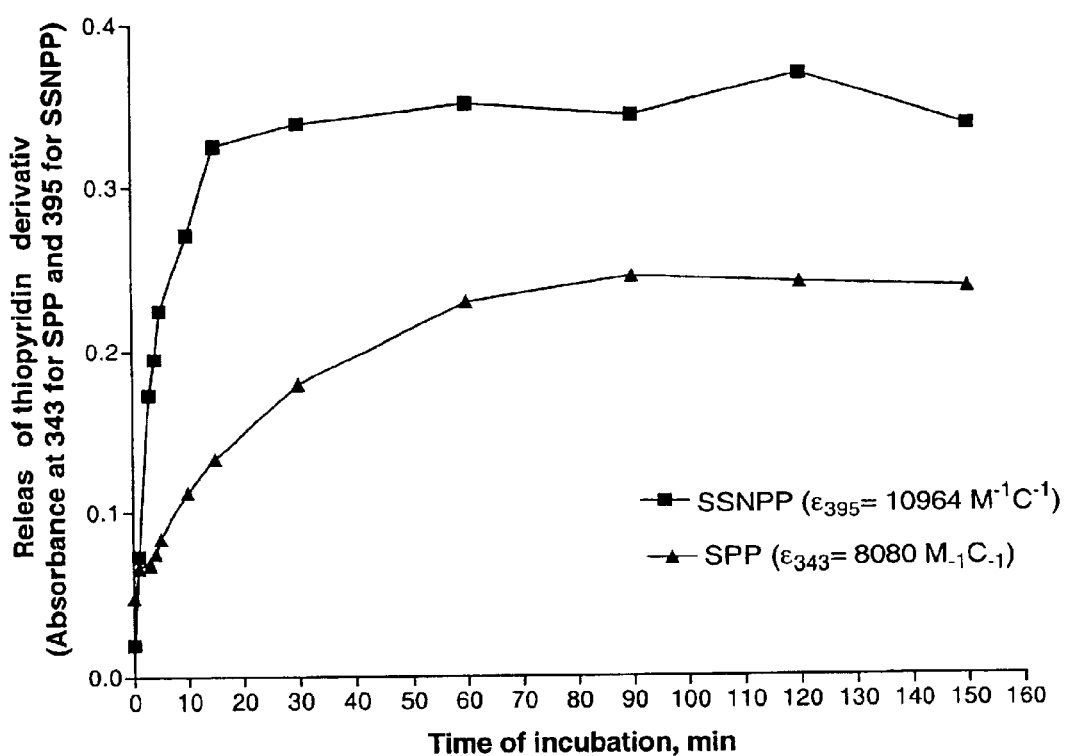

CROSS-LINKERS WITH HIGH REACTIVITY AND SOLUBILITY AND THEIR USE IN THE PREPARATION OF CONJUGATES FOR TARGETED DELIVERY OF SMALL MOLECULE DRUGS

This application claims priority to U.S. provisional application No. 60/403,652, filed Aug. 16, 2002, which is incorporated herein by reference.

FIELD OF THE INVENTION

The present invention relates to an improved method of making conjugates of cell binding agents and small molecule drugs, especially cytotoxic agents.

The present invention also relates to novel bifunctional cross-linkers and methods of making cell binding agents comprising a cross-linker capable of reacting with small molecule drugs. The improved method of making conjugates provides the conjugates with sterically hindered disulfide bonds to enhance in vivo stability of the disulfide link and, unexpectedly, has an increased reaction rate with small molecule drugs bearing a free thiol group. The reaction is about 12-fold faster than with previously described cross-linkers.

BACKGROUND OF THE INVENTION

The bifunctional modification reagent N-succinimidyl 3-(2-pyridyldithio)propionate (SPDP) has been used to link two proteins together through a disulfide bond. The reagent is reacted with the first protein to introduce an active disulfide-containing group in the modification step. A second protein, which contains a free thiol group, is then added to form a disulfide bond between the two proteins in the conjugation step. Many derivatives of SPDP and imide versions of SPDP have been described (U.S. Pat. No. 4,563,304; J. Carlsson et al. 173 *Biochem. J.* 723–737 (1978); Goff D. A., Carroll, S. F. 1 BioConjugate Chem. 381–386 (1990); L. Delprino et al. 82 *J. Pharm. Sci.* 506–512 (1993); S. Arpicco et al., 8 *BioConjugate Chem* 327–337 (1997)).

Conjugates of cell binding agents with highly cytotoxic drugs have been described (U.S. Pat. Nos. 5,208,020 and 5,416,064; R. V. J. Chari et al., 52 *Cancer Res.* 127–131 (1992). In these conjugates, the cell binding agents are first modified with a bifunctional agent such as SPDP to introduce an active disulfide moiety. Reaction with a thiol-containing cytotoxic drug provides a conjugate in which the cell binding agent, such as a monoclonal antibody, and drug are linked via disulfide bonds. In order to enhance the in vivo stability of this disulfide link, it is important to provide sterically hindered disulfide bonds. This objective can be achieved by using cross-linkers that bear one or two methyl substituents on the carbon atom geminal to the disulfide bond or by using drugs bearing one or two methyl substituents on the carbon atom bearing the thiol substituent. However, introduction of such hindered disulfide bonds on cell binding agents or hindered thiols on the drugs results in a marked decrease in the rate of reaction of the thiol-containing drug and the cell binding agent. Thus, processes for the production of conjugates become either impossible, or time consuming and uneconomical. In addition, the extended reaction time causes unwanted dimerization of the thiol-containing drug and consequent loss of reactivity and low yields of product. In the case of monoclonal antibodies and fragments thereof, slow reaction rates of disulfide exchange between the hindered disulfide bond and the thiol-containing drug leads to the undesired side reaction of disulfide bond scission between the heavy and light chains of the antibody or fragment.

Thus there is a need to provide cross-linkers that will provide for an accelerated disulfide exchange reaction rate between the modified cell binding agent and the thiol substituent on the cytotoxic drug. In addition, since cell binding agents, such as monoclonal antibodies, are only soluble in aqueous solutions, it is also desirable to provide cross-linkers that are soluble in water or require only a small percentage (<5% v/v) of an organic solvent to maintain solubility in aqueous solutions.

SUMMARY OF THE INVENTION

The present invention meets these and other objects by providing a method of making a conjugate comprising a cell binding agent and one or more small molecule drugs, wherein said conjugate is represented by formula (V):

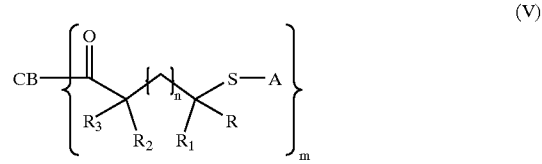

(V)

wherein CB represents the cell binding agent, A represents the small molecule drug linked by a disulfide moiety, R, $R_1$, $R_2$ and $R_3$ are the same or different and are H, methyl, ethyl, or linear, branched or cyclic alkyl having 3 to 6 carbon atoms, n is 0 or an integer from 1 to 4, and m is an integer of 1 to 10 or more, said method comprising:

(1) reacting the cell binding agent with a cross-linker of the formula (I) or (II):

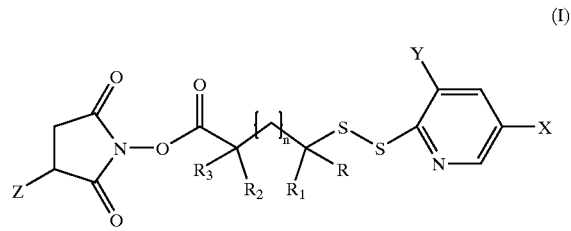

(I)

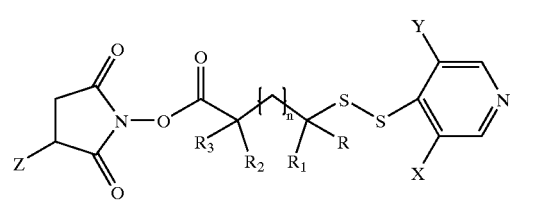

(II)

wherein X and Y are the same or different and are H, $CONR_4R_5$ or $NO_2$, provided that X and Y are not both H at the same time, $R_4$ and $R_5$ are the same or different and are each H, methyl, ethyl, n-propyl, isopropyl, n-butyl, sec-butyl, iso-butyl or tert-butyl, and Z is $SO_3^-M^+$ or H, wherein $M^+$ represents a metal ion or a tetra alkyl ammonium ion, to thereby give a compound of the formula (III) or (IV), respectively:

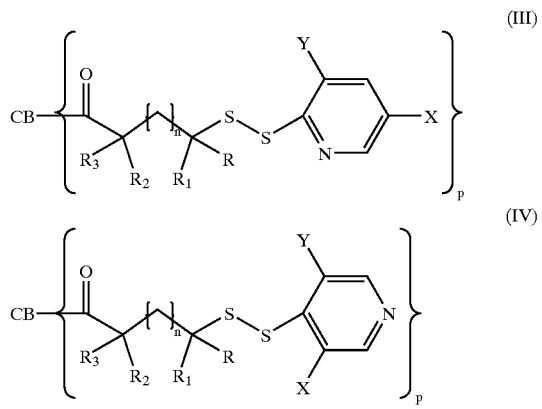

wherein p represents an integer of 1 to 10 or more, and (2) reacting the compound of the formula (III) or (IV) with one or more small molecule drugs comprising a free thiol group.

The invention also provides a method of making a conjugate comprising a cell binding agent and one or more small molecule drugs, wherein said conjugate is represented by formula (V), said method comprising: reacting a compound of the formula (III) or (IV), with one or more small molecule drugs comprising a free thiol group.

In a preferred embodiment, the cell-binding agent is an antibody or antigen binding fragment thereof and the small molecule drug is a cytotoxic agent.

The invention also provides a cross-linker of formula (I) or (II):

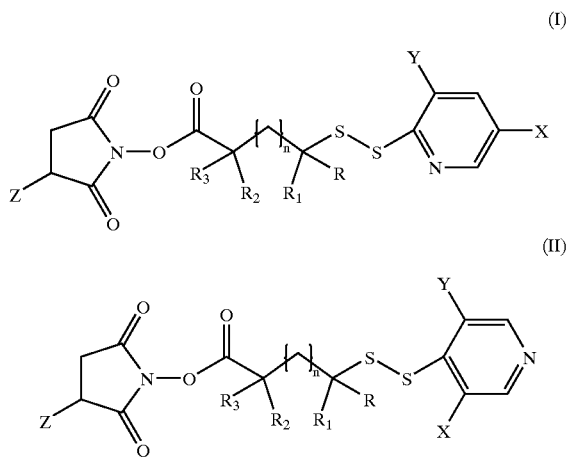

wherein R, $R_1$, $R_2$ and $R_3$ are the same or different and are H, methyl, ethyl, or linear, branched or cyclic alkyl having 3 to 6 carbon atoms, n is 0 or an integer from 1 to 4, X and Y are the same or different and are H, $CONR_4R_5$ or $NO_2$, provided that X and Y are not both H at the same time, $R_4$ and $R_5$ are the same or different and are each H, methyl, ethyl, n-propyl, n-butyl, sec-butyl, iso-butyl or tert-butyl, and Z is $SO_3^-M^+$ or H, wherein $M^+$ represents a metal ion or a tetra alkyl ammonium ion, provided that when X and/or Y is $NO_2$, Z is not H.

The invention further provides a method of making a cell binding agent comprising a linker capable of linking the cell binding agent to a small molecule drug, the cell binding agent comprising a linker being represented by formula (III) or (IV), comprising reacting the cell binding agent with a cross-linker of the formula (I) or (II), respectively.

BRIEF DESCRIPTION OF THE DRAWINGS

FIG. 7 is a comparison of SSNPP and SPP for efficiency of conjugation with increasing drug equivalents in the conjugation reaction. FIG. 7A shows the drug per antibody ratio for various drug equivalents used in the reaction. FIG. 7B shows the efficiency of conjugation for various drug equivalents in the reaction.

FIG. 8 shows the time course for thiol exchange with SSNPP (squares) and SPP (rectangles) linker at pH 7.4. Conjugation was conducted at pH 7.4 using a 1.1-fold molar excess of the maytansinoid, DM1, per linker.

DETAILED DESCRIPTION OF THE INVENTION

Figure 1:
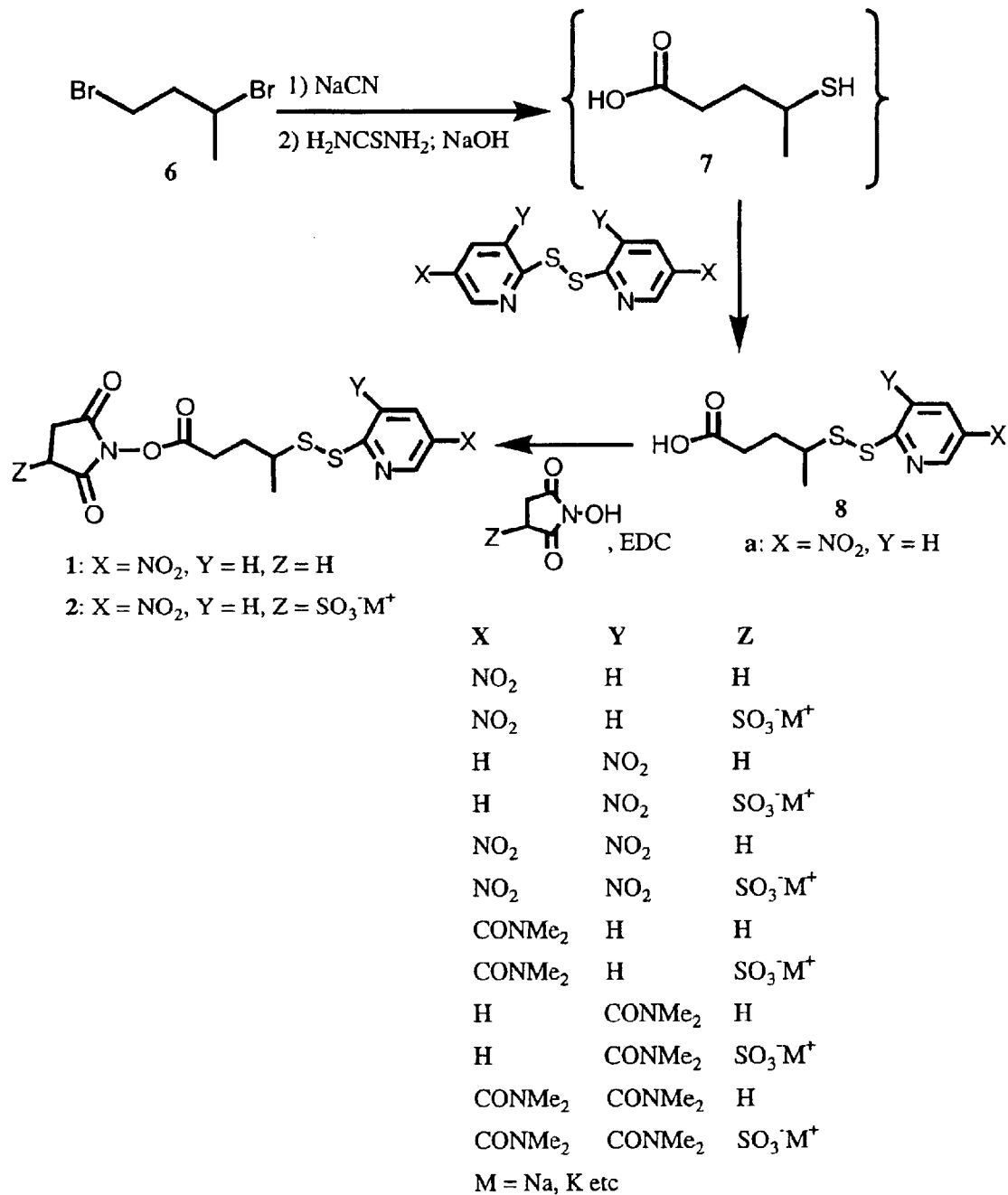
FIG. 1 shows the synthesis of heterobifunctional cross-linking reagents that contain a 2-(nitropyridyl)-disulfide group or a 2-(dinitropyridyl)-disulfide group and a reactive carboxylic acid ester. A mercapto-carboxylic acid compound is first reacted with a 2,2'-di-(nitropyridyl)-disulfide or a 2,2'-di-(dinitropyridyl)-disulfide compound and the carboxylic acid moiety is then esterified with N-hydroxysuccinimide or N-hydroxysulfosuccinimide. As an example, 1,3-dibromobutane was converted to 4-mercaptopentanoic acid, which then was converted to the corresponding cross-linking reagent.

All patents and other publications cited herein are expressly incorporated by reference.

The novel method disclosed herein uses heterobifunctional cross-linkers. Examples of some suitable cross-linkers and their synthesis are shown in FIGS. 1 to 6. Preferably, the cross-linkers are N-succinimidyl 4-(5-nitro-2-pyridyldithio)-pentanoate (1) or the highly water-soluble analog N-sulfosuccinimidyl 4-(5-nitro-2-pyridyldithio)-pentanoate (2), N-succinimidyl-4-(2-pyridyldithio) butyrate (SPDB, 3a), N-succinimidyl-4-(5-nitro-2-pyridyldithio) butyrate (SNPB, 3b), and N-sulfosuccinimidyl-4-(5-nitro-2-pyridyldithio) butyrate (SSNPB, 3c), N-succinimidyl-4-methyl-4-(5-nitro-2-pyridyldithio)pentanoate (SMNP, 4a), N-succinimidyl-4-(5-N,N-dimethylcarboxamido-2-pyridyldithio) butyrate (SCPB, 5a) or N-sulfosuccinimidyl4-(5-N,N-dimethylcarboxamido-2-pyridyldithio) butyrate (SSCPB, Sb). The cell binding agents modified with cross-linkers 1, 2, 3a, 3b, 3c, 4a, 5a or 5b can then react with a small excess of a small molecule drug which contains a thiol moiety to give excellent yields of conjugate. Reaction rates are about 12-fold faster than with the previously described, less reactive cross-linkers. The new reagents have a further advantage that the progress of the disulfide exchange reaction can be monitored readily because of the high extinction coefficient of the nitropyridine-2-thione that is released in the reaction. Lowering the need for excess thiol has the unforeseen benefit of reducing the cleavage of internal disulfide bridges found in native proteins Cross-Linkers The heterobifunctional cross-linkers of the present invention have a two-fold advantage over other cross-linkers in that (1) they allow for formation of a hindered disulfide bond between the cell binding agent and the drug moiety, and (2) they provide for an accelerated disulfide exchange reaction rate with the thiol substituent on the small molecule drug. In addition, the cross-linkers are soluble in water or only require a small percentage (<5% v/v) of an organic solvent to maintain solubility in aqueous solutions.

The heterobifunctional cross-linkers used in the present invention comprise a nitropyridyldithio, dinitropyridyldithio, N,N-dialkylcarboxamidopyridyldithio or di-(N,N-dialkylcarboxamido)pyridyldithio group and a reactive carboxylic ester group such as a N-succinimidyl ester or a N-sulfosuccinimidyl ester group.

Preferably, the cross-linkers are compounds of the formula (I) or (II) below:

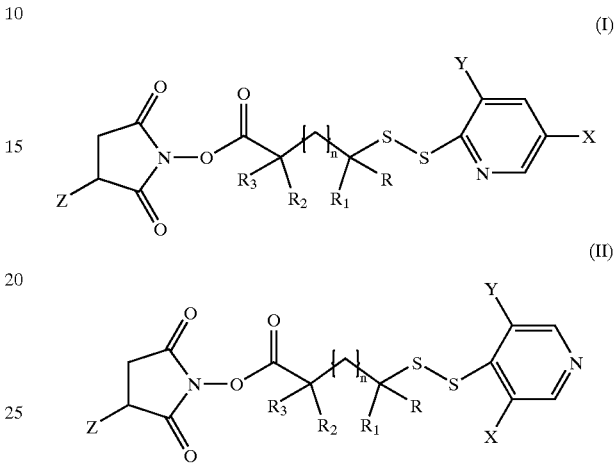

wherein R, $R_1$, $R_2$ and $R_3$ are the same or different and are H, methyl, ethyl, or linear, branched or cyclic alkyl having 3 to 6 carbon atoms, n is 0 or an integer from 1 to 4, X and Y are the same or different and are H, $CONR_4R_5$ or $NO_2$, provided that X and Y are not both H at the same time, $R_4$ and $R_5$ are the same or different and are each H, methyl, ethyl, n-propyl, isopropyl, n-butyl, sec-butyl, iso-butyl or tert-butyl, and Z is $SO_3^-M^+$ or H, wherein $M^+$ represents a metal ion or a tetra alkyl ammonium ion, provided that when X and/or Y is $NO_2$, Z is not H.

Examples of linear, branched or cyclic alkyls having 3 to 6 carbon atoms include propyl, isopropyl, butyl, isobutyl, tert-butyl, pentyl, hexyl, cyclobutyl, cyclopentyl, and cyclohexyl.

Examples of suitable metal ions, $M^+$, include $Li^+$, $Na^+$, $K^+$, and $Rb^+$, and examples of suitable tetra alkyl ammonium ions include tetra methyl ammonium, tetra ethyl ammonium, tetra propyl ammonium, tetra butyl ammonium and tetra alkyl ammonium ions with mixed alkyl groups, such as dimethyl-diethyl ammonium, ethyl-trimethyl ammonium, methyl-ethyl-propyl-butyl ammonium.

In preferred embodiments, both of R and $R_1$ are H or methyl, or one of R and $R_1$ is H and the other is methyl.

In a more preferred embodiment, n is 1, $R_1$ is methyl and R, $R_2$, and $R_3$ are H. In another more preferred embodiment, n is 1 and R, $R_1$, $R_2$, and $R_3$ are H. In a further more preferred embodiment, n is 1, R and $R_1$ are both methyl, and $R_2$ and $R_3$ are both H.

Figure 2:
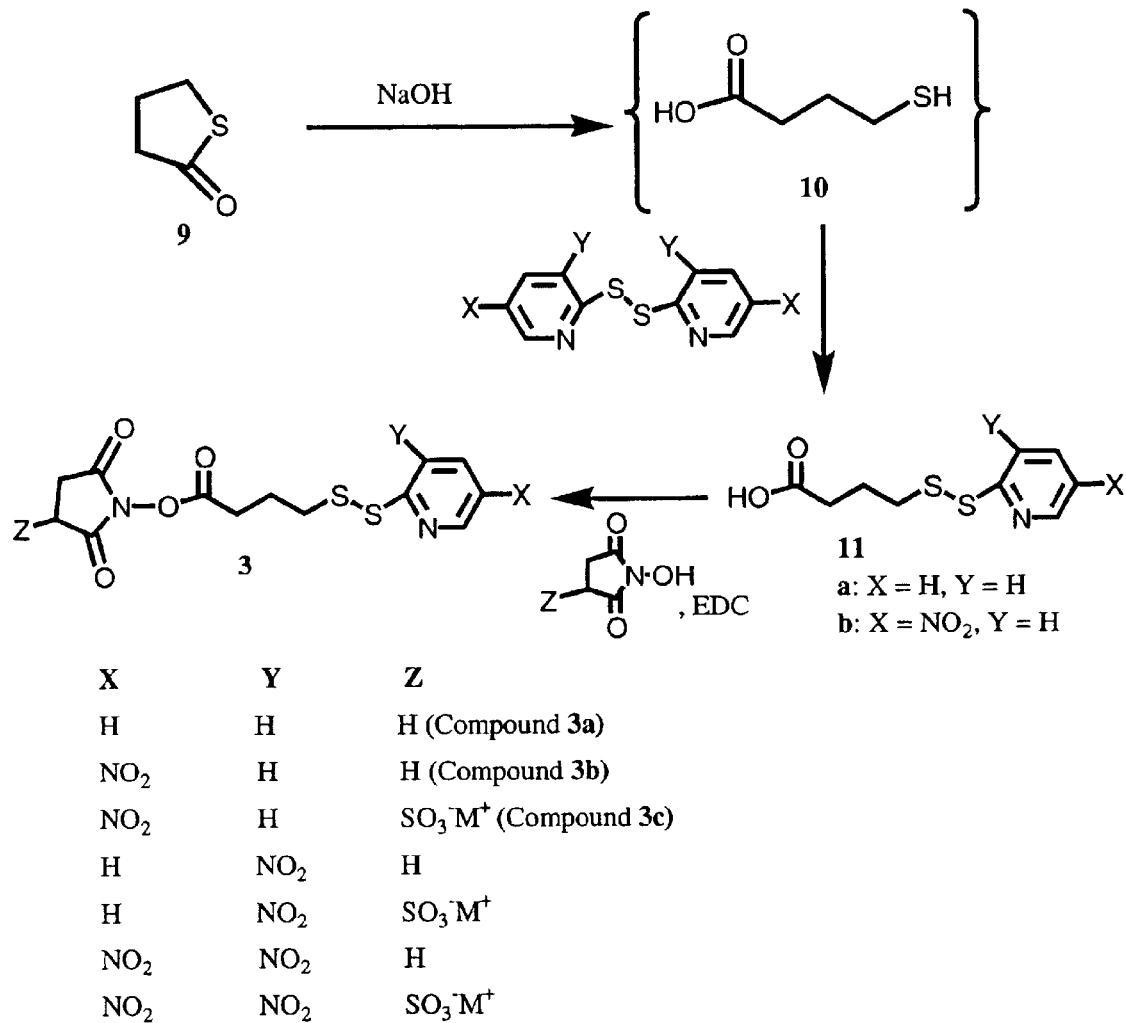
FIG. 2 shows the synthesis of heterobifunctional cross-linking agents N-succinimidyl-4-(2-pyridyldithio) butyrate (SPDB), N-succinimidyl-4-(5-nitro-2-pyridyldithio) butyrate (SNPB) and N-sulfosuccinimidyl-4-(5-nitro-2-pyridyldithio) butyrate (SSNPB), derived from 4-mercaptobutyric acid.
Figure 3:
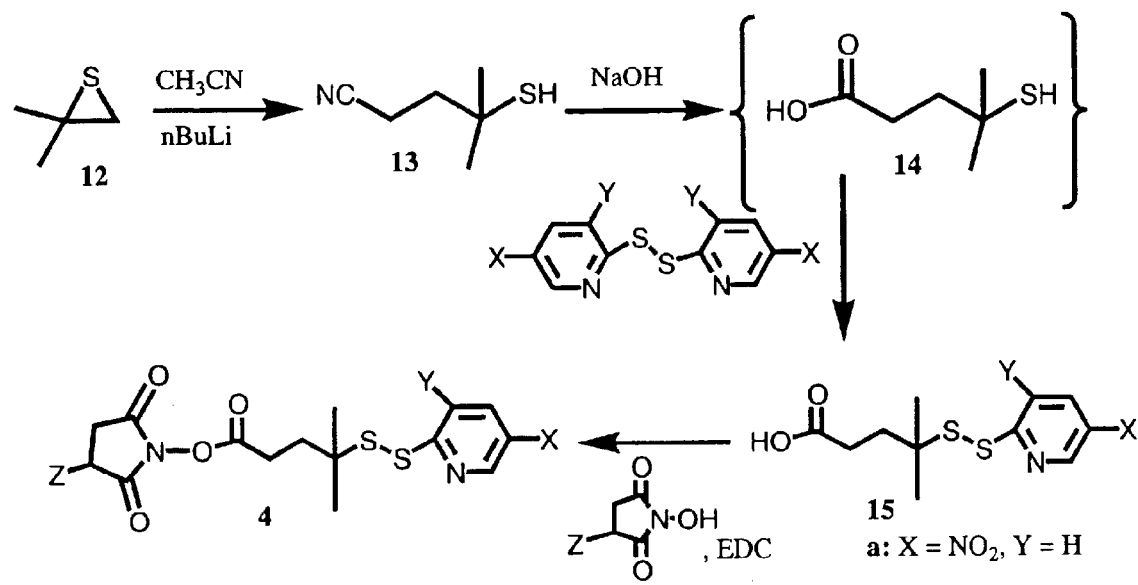
FIG. 3 shows the synthesis of heterobifunctional cross-linking agents N-succinimidyl-4-methyl-4-(5-nitro-2-pyridyldithio)pentanoate (SMNP), and N-sulfosuccinimidyl-4-methyl-4-(5-nitro-2-pyridyldithio) pentanoate (SSMNP)derived from 4-mercapto-4-methyl-pentanoic acid.
Figure 4:
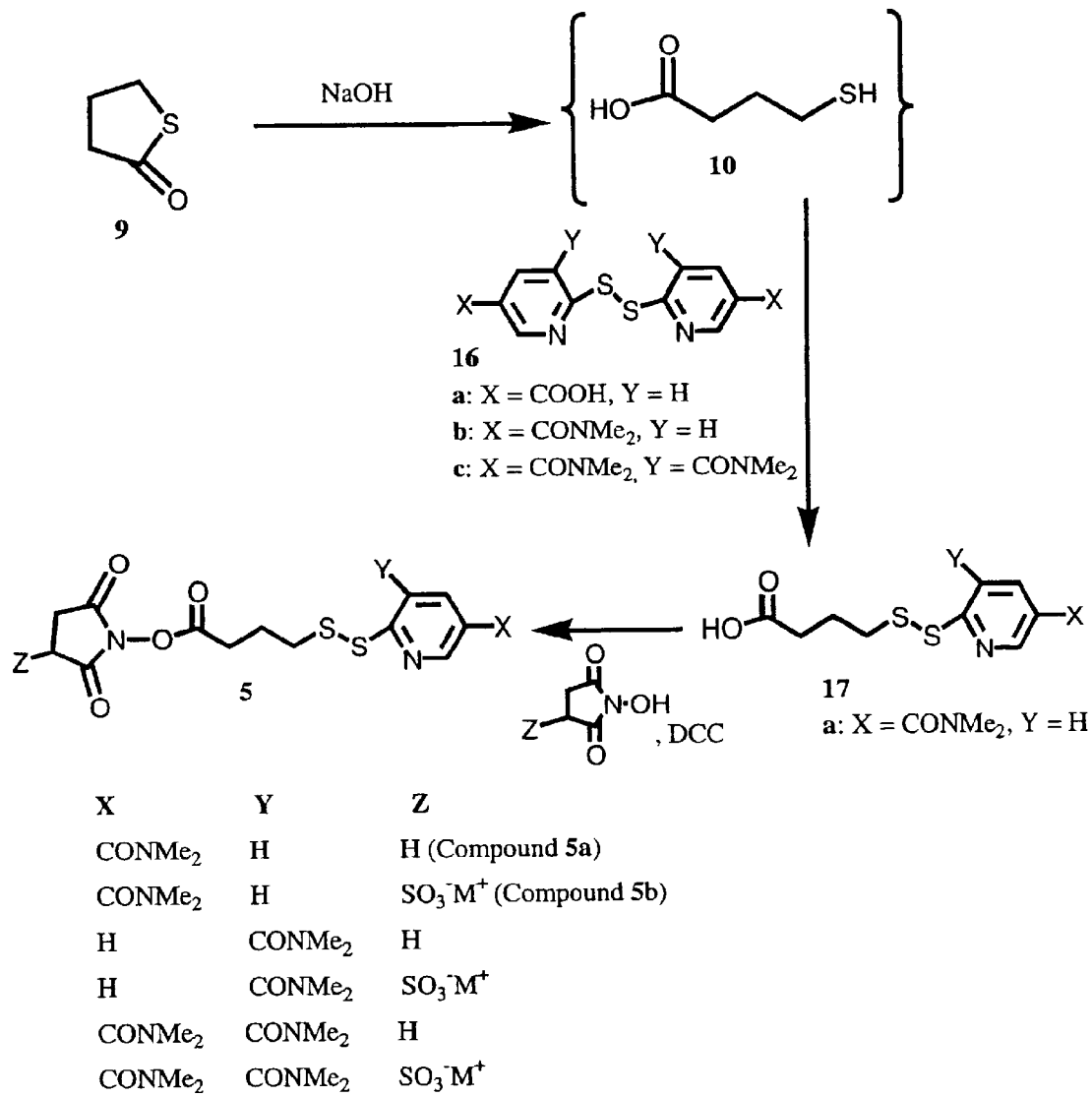
FIG. 4 shows the synthesis of heterobifunctional cross-linking reagents that contain a 2-(N,N-dialkylcarboxamidopyridyl)-disulfide group or a 2-(N,N-dialkylcarboxamidopyridyl)-disulfide group and a reactive carboxylic acid ester. A mercapto-carboxylic acid compound is first reacted with a 2,2'-di-(N,N-dialkylcarboxamidopyridyl)-disulfide compound and the carboxylic acid moiety is then esterified with N-hydroxysuccinimide or N-hydroxysulfosuccinimide. As an example, the synthesis of heterobifunctional cross-linking agents N-succinimidyl-4-(5-N,N-dimethylcarboxamido-2-pyridyldithio) butyrate (SCPB) and N-sulfosuccinimidyl-4-(5-N,N-dimethylcarboxamido-2-pyridyldithio) butyrate (SSCPB), derived from 6,6-dithiodinicotinic acid are shown.
Figure 5:
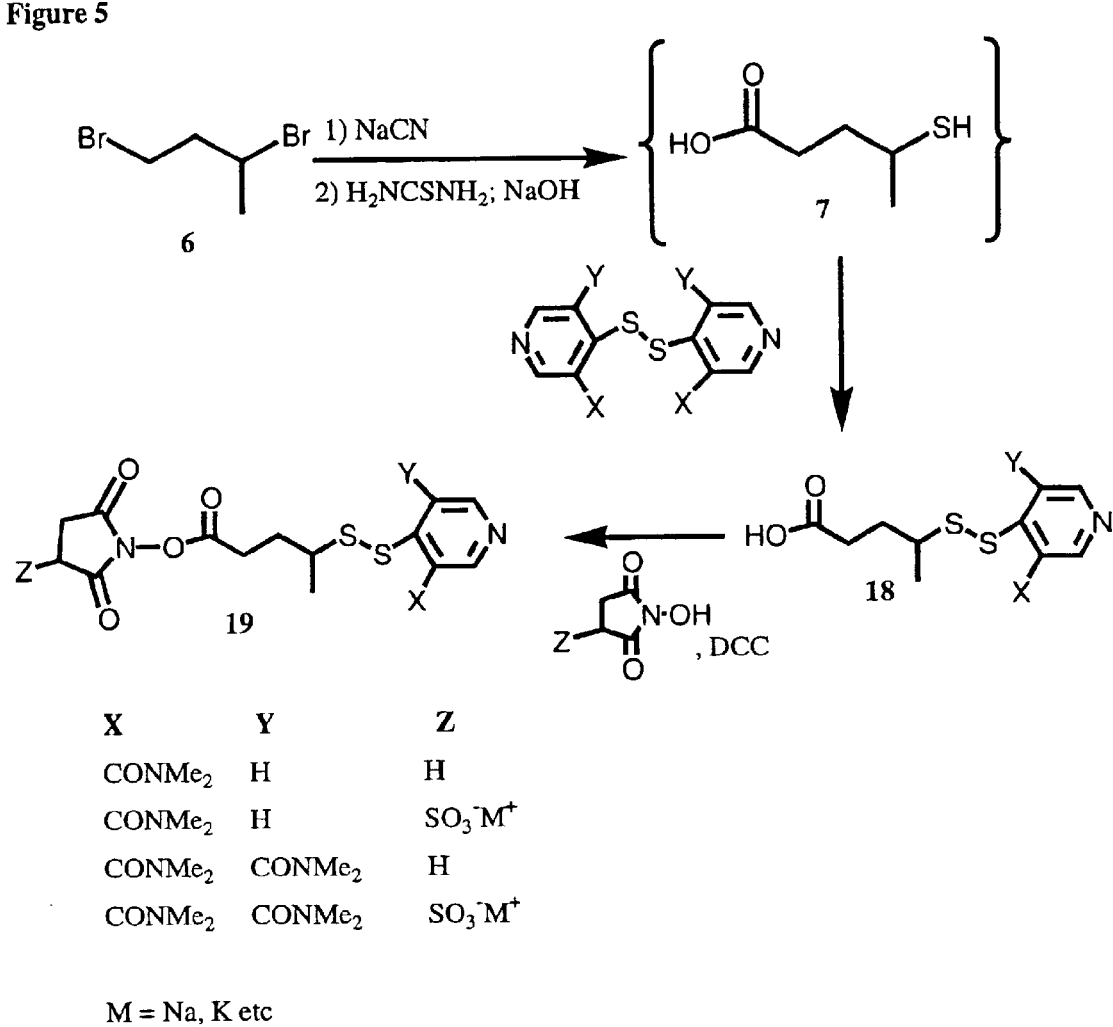
FIG. 5 shows the synthesis of heterobifunctional cross-linking reagents that contain a 4-(N,N-dialkylcarboxamidopyridyl)-disulfide group or a 4-(N,N-dialkylcarboxamidopyridyl)-disulfide group and a reactive carboxylic acid ester. A mercapto-carboxylic acid compound is first reacted with a 4,4'-di-(N,N-dialkylcarboxamidopyridyl)-disulfide compound and the carboxylic acid moiety is then esterified with N-hydroxysuccinimide or N-hydroxysulfosuccinimide. As an example, the synthesis of heterobifunctional cross-linking agents N-succinimidyl-4-(5-N,N-dimethylcarboxamido-4-pyridyldithio) butyrate and N-sulfosuccinimidyl-4-(5-N,N-dimethylcarboxamido-4-pyridyldithio) butyrate is shown.
Figure 6:
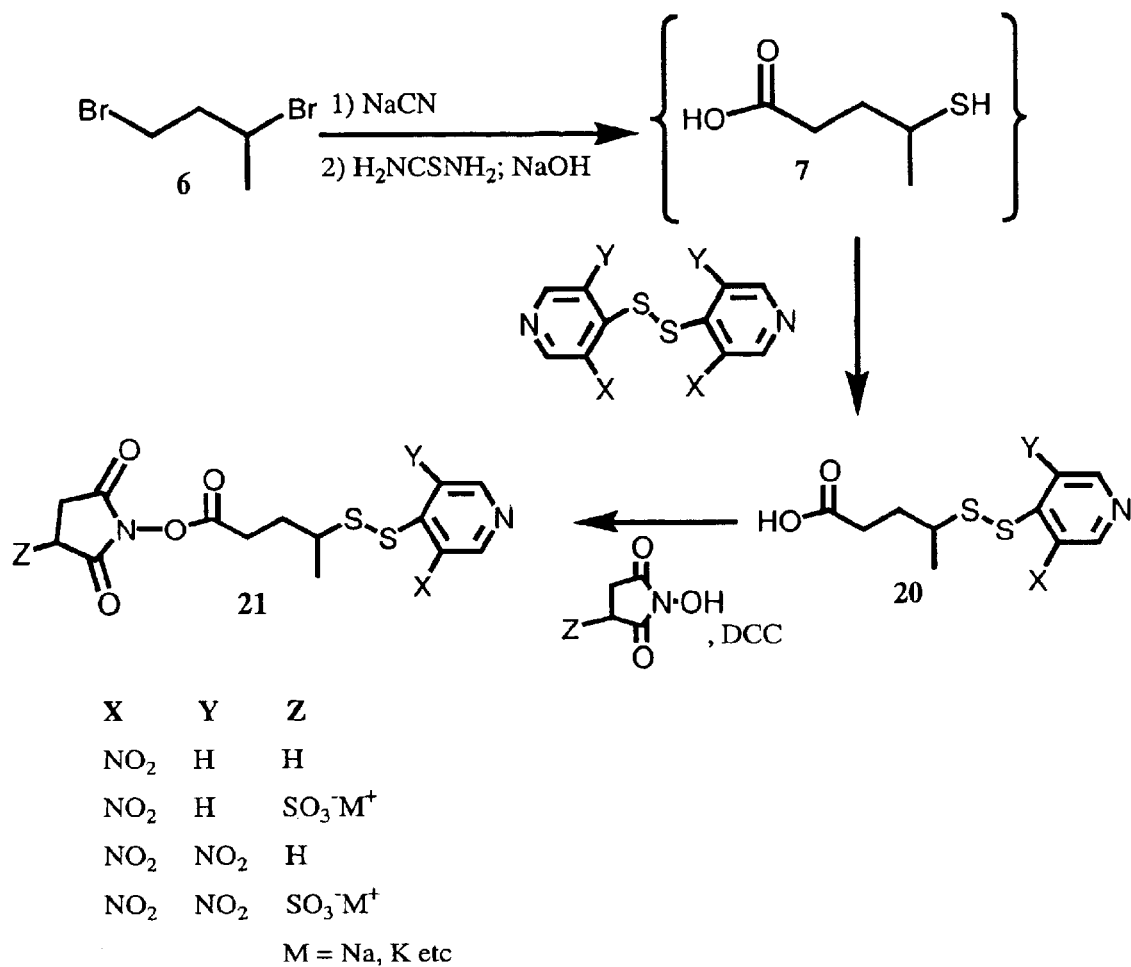
FIG. 6 shows the synthesis of heterobifunctional cross-linking reagents that contain a 4-(nitropyridyl)-disulfide group or a 4-(dinitropyridyl)-disulfide group and a reactive carboxylic acid ester. A mercapto-carboxylic acid compound is first reacted with a 4,4'-di-(nitropyridyl)-disulfide or a 4,4'-di-(dinitropyridyl)-disulfide compound and the carboxylic acid moiety is then esterified with N-hydroxysuccinimide or N-hydroxysulfosuccinimide. As an example, 1,3-dibromobutane was converted to 4-mercaptopentanoic acid, which then was converted to the corresponding cross-linking reagents.

The synthesis of 2-dithionitropyridyl and 2-dithiodinitropyridyl containing cross-linkers of formulae (I) is shown in FIGS. 1, 2 and 3 and the synthesis of the corresponding 4-dithionitropyridyl and 4-dithio-dinitropyridyl containing cross-linkers of the formula (II) is shown in FIG. 6. The synthesis of 2-dithio-N,N-dimethylcarboxamidopyridyl containing cross-linkers of formulae (I) is shown in FIG. 4 and the synthesis of the corresponding 4-dithio-N,N-dimethylcarboxamidopyridyl containing cross-linkers of formulae (II) is shown in FIG. 5.

A mercapto acid is reacted with dithiobis(nitropyridine), dithiobis(dinitropyridine), or dithiobis(dimethylcarboxamidopyridine), in an organic solvent, preferably a polar organic solvent, such as tetrahydrofuran, either with or without base, but preferably with a base such as triethyl amine. The resulting unsymmetric disulfide acid is then reacted with either N-hydroxysuccinimide or N-hydroxysulfosuccinimide in an organic solvent, preferably a polar aprotic organic solvent, such as dimethyl formamide, in the presence of a coupling agent, preferably a carbodiimide such as dicylohexylcarbodiimide, to give the desired compound.

In preferred embodiments, both of R and $R_1$ are H or methyl, or one of R and $R_1$ is H and the other is methyl.

In a more preferred embodiment, n is 1, $R_1$ is methyl and R, $R_2$, and $R_3$ are H. In another more preferred embodiment, n is 1 and R, $R_1$, $R_2$, and $R_3$ are H. In a further more preferred embodiment, n is 1, R and $R_1$ are both methyl, and $R_2$ and $R_3$ are both H.

The present invention also provides novel cross-linkers of the formula (I) or (II), shown above, wherein R, $R_1$, $R_2$ and $R_3$ are the same or different and are H, methyl, ethyl, or linear, branched or cyclic alkyl having 3 to 6 carbon atoms, n is 0 or an integer from 1 to 4, X and Y are the same or different and are $CONR_4R_5$ or $NO_2$, $R_4$ and $R_5$ are the same or different and are each H, methyl, ethyl, n-propyl, isopropyl, n-butyl, sec-butyl, iso-butyl or tert-butyl, and Z is $SO_3^-M^+$ or H, wherein $M^+$ represents a metal ion or a tetra alkyl ammonium ion, provided that when X and/or Y is $NO_2$, Z is not H.

Cell Binding Agents Bearing a Disulfide-Containing Cross-Linker

The cell-binding agent bearing a cross-linker with a reactive group is preferably represented by the formula (III) or (IV):

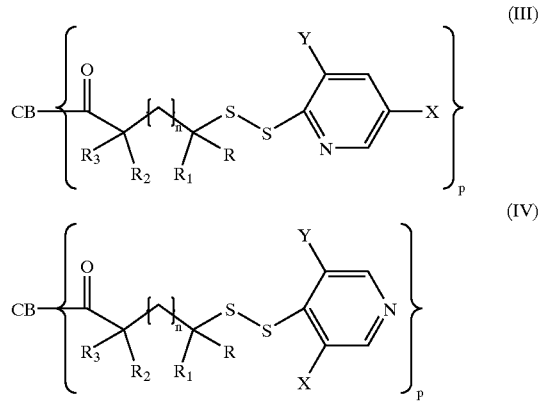

wherein CB represents a cell binding agent, R, $R_1$, $R_2$ and $R_3$ are the same or different and are H, methyl, ethyl, or linear, branched or cyclic alkyl having 3 to 6 carbon atoms, n is 0 or an integer from 1 to 4, X and Y are the same or different and are H, $CONR_4R_5$ or $NO_2$, provided that X and Y are not both H at the same time, $R_4$ and $R_5$ are the same or different and are each H, methyl, ethyl, n-propyl, isopropyl, n-butyl, sec-butyl, iso-butyl or tert-butyl, and p represents an integer of 1 to 10 or more.

In preferred embodiments, both of R and $R_1$ are H or methyl, or one of R and $R_1$ is H and the other is methyl.

In a more preferred embodiment, n is 1, $R_1$ is methyl and R, $R_2$, and $R_3$ are H. In another more preferred embodiment, n is 1 and R, $R_1$, $R_2$, and $R_3$ are H. In a further more preferred embodiment, n is 1, R and $R_1$ are both methyl, and $R_2$ and $R_3$ are both H.

The cell-binding agent bearing a cross-linker can be synthesized by methods known in the art (U.S. Pat. Nos. 6,340,701 B1, 5,846,545, 5,585,499, 5,475,092, 5,414,064, 5,208,020, and 4,563,304; R. V. J. Chari et al. Cancer Research 52, 127–131, 1992; R. V. J. Chari et al. Cancer Research 55, 4079–4084, 1995; J. Carlsson et al. 173 *Biochem. J.* (1978) 723–737(1978); Goff D. A., Carroll, S. F. 1 BioConjugate Chem. 381–386 (1990); L. Delprino et al. 82 *J. Pharm. Sci.* 506–512 (1993); S. Arpicco et al., 8 *BioConjugate Chem* 327–337 (1997)). Advantageously, because the cross-linker groups are soluble in water or require only a small percentage of organic solvent to maintain solubility in aqueous solution, the reaction between the cell-binding agent and the cross-linker can be conducted in aqueous solution. The cross-linking reagent is dissolved in a polar organic solvent that is missible with water, for example different alcohols, such as methanol, ethanol, and propanol, dimethyl formamide, dimethyl acetamide, or dimethylsulfoxide at a high concentration, for example 1–100 mM, and then an appropriate aliquot is added to the buffered aqueous solution of the cell-binding agent. An appropriate aliquot is an amount of solution that introduces 1–10 cross-linking groups per cell-binding agent, preferably 2–5 groups, and the volume to be added should not exceed 10%, preferably 5%, and most preferably 1–3% of the volume of the cell-binding agent solution. The aqueous solutions for the cell-binding agents are buffered between pH 6 and 9, preferably between 6.5 and 7.5 and can contain any non-nucleophilic buffer salts useful for these pH ranges. Typical buffers include phosphate, triethanolamine.HCl, HEPES, and MOPS buffers, which can contain additional components, such as sucrose and salts, for example, NaCl. After the addition the reaction is incubated at a temperature of from 4° C. to 40° C., preferably at ambient temperature. The progress of the reaction can be monitored by measuring the incease in the absorption at 495 nm or another appropriate wavelength. After the reaction is complete, isolation of the modified cell-binding agent can be performed in a routine way, using for example gel filtration chromatography, or adsorptive chromatography.

The extent of modification can be assessed by measuring the absorbance of the nitropyridine thione, dinitropyridine dithione, carboxamidopyridine dithione or dicarboxamidopyridine dithione group released.

The cell-binding agent that comprises the conjugates of the present invention may be of any kind presently known, or that become known, and include peptides and non-peptides. The cell-binding agent may be any compound that can bind a cell, either in a specific or non-specific manner. Generally, these can be antibodies (especially monoclonal antibodies and antibody fragments), interferons, lymphokines, hormones, growth factors, vitamins, nutrient-transport molecules (such as transferrin), or any other cell-binding molecule or substance.

More specific examples of cell-binding agents that can be used include:

resurfaced antibodies (U.S. Pat. No. 5,639,641);

fragments of antibodies such as sFv, Fab, Fab', and F(ab')₂ (Parham, *J. Immunol.* 131:2895–2902 (1983); Spring et al, *J. Immunol.* 113:470–478 (1974); Nisonoff et al, *Arch. Biochem. Biophys.* 89:230–244 (1960));

interferons (e.g. α, β, γ);

lymphokines such as IL-2, IL-3, IL-4, IL-6;

hormones such as insulin, TRH (thyrotropin releasing hormones), MSH (melanocyte-stimulating hormone), steroid hormones, such as androgens and estrogens;

vitamins such as folic acid;

growth factors and colony-stimulating factors such as EGF, TGF-α, G-CSF, M-CSF and GM-CSF (Burgess, *Immunology Today* 5:155–158 (1984)); and transferrin (O'Keefe et al, *J. Biol. Chem.* 260:932–937 (1985)).

Monoclonal antibody techniques allow for the production of extremely specific cell-binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of sFv (single chain variable region), specifically human sFv (see, e.g., Griffiths et al, U.S. Pat. No. 5,885,793; McCafferty et al, WO 92/01047; Liming et al, WO 99/06587.)

Selection of the appropriate cell-binding agent is a matter of choice that depends upon the particular cell population that is to be targeted, but in general monoclonal antibodies and epitope binding fragments thereof are preferred, if an appropriate one is available.

For example, the monoclonal antibody My9 is a murine IgG$_{2a}$ antibody that is specific for the CD33 antigen found on Acute Myeloid Leukemia (AML) cells (Roy et al. *Blood* 77:2404–2412 (1991)) and can be used to treat AML patients. Similarly, the monoclonal antibody anti-B4 is a murine IgG$_1$, that binds to the CD19 antigen on B cells (Nadler et al, *J. Immunol.* 131:244–250 (1983)) and can be used if the target cells are B cells or diseased cells that express this antigen such as in non-Hodgkin's lymphoma or chronic lymphoblastic leukemia. Similarly, the antibody N901 is a murine monoclonal IgG$_1$ antibody that binds to CD56 found on small cell lung carcinoma cells and on cells of other tumors of neuroendocrine origin (Roy et al. *J. Nat. Cancer Inst.* 88:1136–1145 (1996)).

Additionally, GM-CSF, which binds to myeloid cells, can be used as a cell-binding agent to diseased cells from acute myelogenous leukemia. IL-2, which binds to activated T-cells, can be used for prevention of transplant graft rejection, for therapy and prevention of graft-versus-host disease, and for treatment of acute T-cell leukemia. MSH, which binds to melanocytes, can be used for the treatment of melanoma. Folic acid, which targets the folate receptor expressed on ovarian and other cancers is also a suitable cell-binding agent.

Cancers of the breast and testes can be successfully targeted with estrogen (or estrogen analogues) or androgen (or androgen analogues), respectively, as cell-binding agents.

The new method is especially advantageous when the cell-binding agent is an antibody or fragment thereof, because the incresased rate of the disulfide exchange between the hindered disulfide bond and the thiol-containing drug reduces the extent of the undesired side-reaction of disulfide bond scission between the heavy and light chains of the antibody or fragment.

Cytotoxic Conjugates

The cytotoxic conjugates of the present invention each comprises one or more small molecule drugs covalently bonded to a cell-binding agent through a cross-linker as described above. Preferably, the cytotoxic conjugates have the following formula (V):

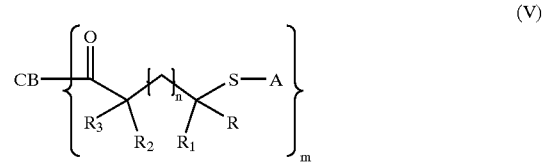

wherein CB represents the cell binding agent, A represents the small molecule drug linked by a disulfide moiety, R, R$_1$, R$_2$ and R$_3$ are the same or different and are H, methyl, ethyl, or linear, branched or cyclic alkyl having 3 to 6 carbon atoms, as defined above, n is 0 or an integer from 1 to 4, and m is 1 to 10 or more.

In preferred embodiments, both of R and R$_1$ are H or methyl, or one of R and R$_1$ is H and the other is methyl.

In a more preferred embodiment, n is 1, R$_1$ is methyl and R, R$_2$, and R$_3$ are H. In another more preferred embodiment, n is 1 and R, R$_1$, R$_2$, and R$_3$ are H. In a further more preferred embodiment, n is 1, R and R$_1$ are both methyl, and R$_2$ and R$_3$ are both H.

Preferably the number of small molecule drugs bound to each cell-binding agent is 1–10, more preferably 2–5, and even more preferably 3–4.

Synthesis of the conjugates involves a disulfide exchange between the disulfide bond in the cross-linker covalently bonded to the cell-binding agent and a small molecule drug containing a free thiol group. The reaction results in a conjugate in which the cell-binding agent and the small molecule drugs are linked through sterically hindered disulfide bonds. Importantly, when the reaction is conducted using cell binding agents modified to contain the cross-linkers of the present invention, unexpectedly, the disulfide exchange reaction (at room temperature and pH 6.5–7.5) occurs up to twelve times faster than when other cross-linkers are used.

The cytotoxic conjugate may be purified by standard biochemical means, such as gel filtration on a Sephadex G25 or Sephacryl S 300 column, or by dialysis as previously described.

Small Molecule Drugs

The small molecule drugs useful in the method include any small molecule drug that has a thiol group for linking to the cell binding agent. The invention includes known drugs as well as those that may become known. Especially preferred small molecule drugs include cytotoxic agents.

The cytotoxic agent may be any compound that results in the death of a cell, or induces cell death, or in some manner decreases cell viability, wherein each cytotoxic agent comprises a thiol moiety. Preferred cytotoxic agents are maytansinoid compounds, taxane compounds, CC-1065 compounds, daunorubicin compounds and doxorubicin compounds, and analogues and derivatives thereof, some of which are described below.

Maytansinoids

Maytansinoids that can be used in the present invention are well known in the art and can be isolated from natural sources according to known methods or prepared synthetically according to known methods.

Examples of suitable maytansinoids include maytansinol and maytansinol analogues. Examples of suitable maytansinol analogues include those having a modified aromatic ring and those having modifications at other positions.

Specific examples of suitable analogues of maytansinol having a modified aromatic ring include:

(1) C-19-dechloro (U.S. Pat. No. 4,256,746) (prepared by LAH reduction of ansamytocin P2);

(2) C-20-hydroxy (or C-20-demethyl)+/−C-19-dechloro (U.S. Pat. Nos. 4,361,650 and 4,307,016) (prepared by demethylation using Streptomyces or Actinomyces or dechlorination using LAH); and (3) C-20-demethoxy, C-20-acyloxy (—OCOR), +/−dechloro (U.S. Pat. No. 4,294,757) (prepared by acylation using acyl chlorides).

Specific examples of suitable analogues of maytansinol having modifications of other positions include:

(1) C-9-SH (U.S. Pat. No. 4,424,219) (prepared by the reaction of maytansinol with $H_2S$ or $P_2S_5$);

(2) C-14-alkoxymethyl (demethoxy/$CH_2OR$) (U.S. Pat. No. 4,331,598);

(3) C-14-hydroxymethyl or acyloxymethyl ($CH_2OH$ or $CH_2OAc$) (U.S. Pat. No. 4,450,254) (prepared from Nocardia);

(4) C-15-hydroxy/acyloxy (U.S. Pat. No. 4,364,866) (prepared by the conversion of maytansinol by Streptomyces);

(5) C-15-methoxy (U.S. Pat. Nos. 4,313,946 and 4,315,929) (isolated from *Trewia nudiflora*);

(6) C-18-N-demethyl (U.S. Pat. Nos. 4,362,663 and 4,322,348) (prepared by the demethylation of maytansinol by Streptomyces); and (7) 4,5-deoxy (U.S. Pat. No. 4,371,533) (prepared by the titanium trichloride/LAH reduction of maytansinol).

The synthesis of thiol-containing maytansinoids useful in the present invention is fully disclosed in U.S. Pat. Nos. 5,208,020 and 5,416,064, incorporated herein in their entirety.

Maytansinoids with a thiol moiety at the C-3 position, the C-14 position, the C-15 position or the C-20 position are all expected to be useful. The C-3 position is preferred and the C-3 position of maytansinol is especially preferred. Also preferred is an N-methyl-alanine-containing C-3 thiol moiety maytansinoid, and an N-methyl-cysteine-containing C-3 thiol moiety maytansinoid, and analogues of each.

Specific examples of N-methyl-alanine-containing C-3 thiol moiety maytansinoid derivatives useful in the present invention are represented by the formulae M1, M2, M3, M6 and M7.

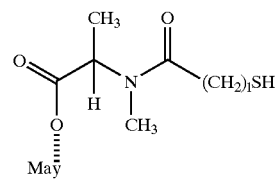

M1 wherein:

l is an integer of from 1 to 10; and
may is a maytansinoid.

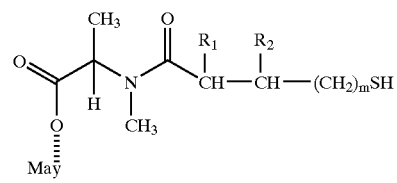

M2 wherein:

$R_1$ and $R_2$ are H, $CH_3$ or $CH_2CH_3$, and may be the same or different;
m is 0, 1, 2 or 3; and
may is a maytansinoid.

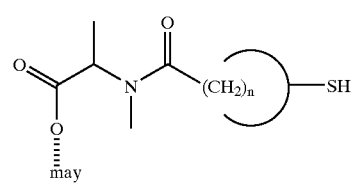

M3 wherein:

n is an integer of from 3 to 8; and
may is a maytansinoid.

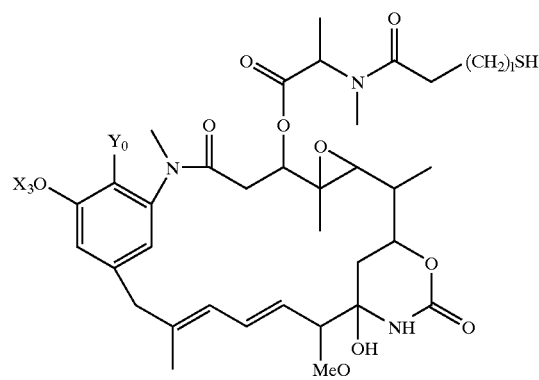

M6 wherein:

l is 1, 2 or 3;
$Y_0$ is Cl or H; and
$X_3$ is H or $CH_3$.

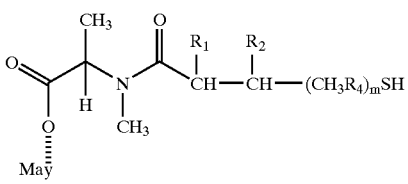

M7 wherein:

$R_1$, $R_2$, $R_3$, $R_4$ are H, $CH_3$ or $CH_2CH_3$, and may be the same or different;
m is 0, 1, 2 or 3; and
may is a maytansinoid.

Specific examples of N-methyl-cysteine-containing C-3 thiol moiety maytansinoid derivatives useful in the present invention are represented by the formulae M4 and M5.

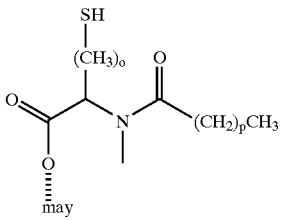

M4 wherein:

o is 1, 2 or 3;
p is an integer of 0 to 10; and
may is a maytansinoid.

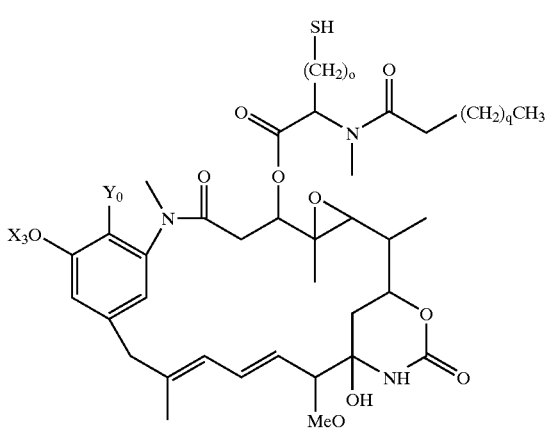

M5 wherein:

o is 1, 2 or 3;
q is an integer of from 0 to 10;
$Y_0$ is Cl or H; and
$X_3$ is H or $CH_3$.

Taxanes

The cytotoxic agent according to the present invention, may also be a taxane.

Taxanes that can be used in the present invention have been modified to contain a thiol moiety. Some taxanes useful in the present invention have the formula T1 shown below:

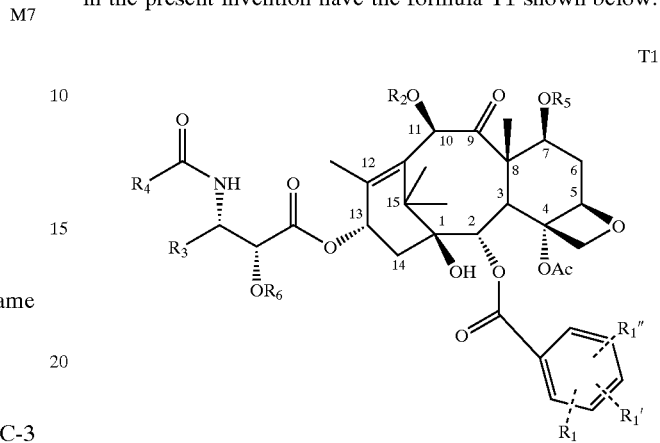

T1

Four embodiments of these novel taxanes are described below.

In embodiments (1), (2), (3), and (4), $R_1$, $R_1'$, and $R_1''$ are the same or different and are H, an electron withdrawing group, such as F, $NO_2$, CN, Cl, $CHF_2$, or $CF_3$ or an electron donating group, such as $-OCH_3$, $-OCH_2CH_3$, $-NR_7R_8$, $-OR_9$, wherein $R_7$ and $R_8$ are the same or different and are linear, branched, or cyclic alkyl groups having 1 to 10 carbon atoms or simple or substituted aryl having 1 to 10 carbon atoms. Preferably the number of carbon atoms for $R_7$ and $R_8$ is 1 to 4. Also, preferably $R_7$ and $R_8$ are the same. Examples of preferred $-NR_7R_8$ groups include dimethyl amino, diethyl amino, dipropyl amino, and dibutyl amino, where the butyl moiety is any of primary, secondary, tertiary or isobutyl. $R_9$ is linear, branched or cyclic alkyl having 1 to 10 carbon atoms.

$R_1$ preferably is $OCH_3$, F, $NO_2$, or $CF_3$.

Also preferably, $R_1$ is in the meta position and $R_1'$ and $R_1''$ are H or $OCH_3$.

$R_2$ in embodiments (1), (2) and (4), is H, heterocyclic, a linear, branched, or cyclic ester having from 1 to 10 carbon atoms or heterocyclic, a linear, branched, or cyclic ether having from 1 to 10 carbon atoms or a carbamate of the formula $-CONR_{10}R_{11}$, wherein $R_{10}$ and $R_{11}$ are the same or different and are H, linear, branched, or cyclic alkyl having 1 to 10 atoms or simple or substituted aryl having 1 to 10 carbon atoms. For esters, preferred examples include $-COCH_2CH_3$ and $-COCH_2CH_2CH_3$. For ethers, preferred examples include $-CH_2CH_3$ and $-CH_2CH_2CH_3$. For carbamates, preferred examples include $-CONHCH_2CH_3$, $-CONHCH_2CH_2CH_3$, $-CO$-morpholino, $-CO$-piperazino, $-CO$-piperidino, or $-CO-N$-methylpiperazino.

$R_2$ in embodiment (3), is a thiol-containing moiety.

$R_3$ in embodiments (1), (3) and (4), is aryl, or is linear, branched or cyclic alkyl having 1 to 10 carbon atoms, preferably $-CH_2CH(CH_3)_2$.

$R_3$ in embodiment (2), is $-CH=C(CH_3)_2$.

$R_4$ in all four embodiments, is $-OC(CH_3)_3$ or $-C_6H_5$.

$R_5$ in embodiments (1) and (2), is a thiol-containing moiety and $R_6$ has the same definition as above for $R_2$ for embodiments (1), (2) and (4).

$R_5$ and $R_6$ in embodiment (3), are the same or different, and have the same definition as above for $R_2$ for embodiments (1), (2) and (4).

$R_5$ in embodiment (4), has the same definition as above for $R_2$ for embodiments (1), (2) and (4) and $R_6$ is a thiol moiety.

The preferred positions for introduction of the thiol-containing moiety are $R_2$ and $R_5$, with $R_2$ being the most preferred.

The side chain carrying the thiol moiety can be linear or branched, aromatic or heterocyclic. One of ordinary skill in the art can readily identify suitable side chains. Specific examples of thiol moieties include —$(CH_2)_n SH$, —$CO(CH_2)_n SH$, —$(CH_2)_n CH(CH_3)SH$, —$CO(CH_2)_n CH(CH_3)SH$, —$(CH_2)_n C(CH_3)_2 SH$, —$CO(CH_2)_n C(CH_3)_2 SH$, —$CONR_{12}(CH_2)_n SH$, —$CONR_{12}(CH_2)_n CH(CH_3)SH$, or —$CONR_{12}(CH_2)_n C(CH_3)_2 SH$, —CO-morpholino-XSH, —CO-piperazino-XSH, —CO-piperidino-XSH, and —CO—N-methylpiperazino-XSH wherein X is a linear alkyl or branched alkyl having 1–10 carbon atoms.

$R_{12}$ is a linear alkyl, branched alkyl or cyclic alkyl having 1 to 10 carbon atoms, or simple or substituted aryl having from 1 to 10 carbon atoms or heterocyclic, and can be H, and n is an integer of 0 to 10.

Examples of linear alkyls include methyl, ethyl, propyl, butyl, pentyl and hexyl.

Examples of branched alkyls include isopropyl, isobutyl, sec.-butyl, tert.-butyl, isopentyl and 1-ethyl-propyl.

Examples of cyclic alkyls include cyclopropyl, cyclobutyl, cyclopentyl and cyclohexyl.

Examples of simple aryls include phenyl and naphthyl.

Examples of substituted aryls include aryls such as those described above substituted with alkyl groups, with halogens, such as Cl, Br, F, nitro groups, amino groups, sulfonic acid groups, carboxylic acid groups, hydroxy groups or alkoxy groups.

Examples of heterocyclics are compounds wherein the heteroatoms are selected from O, N, and S, and include morpholino, piperidino, piperazino, N-methylpiperazino, pyrrollyl, pyridyl, furyl and thiophene.

The taxanes having a thiol moiety can be synthesized according to known methods. The starting material for the synthesis is the commercially available 10-deacetylbaccatin III. The chemistry to introduce various substituents is described in several publications (Ojima et al, *J. Med. Chem.* 39:3889–3896 (1996); Ojima et al., *J. Med. Chem.* 40:267–278 (1997); Ojima et al., *Proc. Natl. Acad. Sci.,* 96:4256–4261 (1999); U.S. Pat. No. 5,475,011 and U.S. Pat. No. 5,811,452).

The substituent $R_1$ on the phenyl ring and the position of the substituent $R_1$ can be varied until a compound of the desired toxicity is obtained. Furthermore, the degree of substitution on the phenyl ring can be varied to achieve a desired toxicity. That is, the phenyl ring can have one or more substituents (e.g., mono-, di-, or tri-substitution of the phenyl ring) which provide another means for achieving a desired toxicity. One of ordinary skill in the art can determine the appropriate chemical moiety for $R_1$ and the appropriate position for $R_1$ using only routine experimentation.

For example, electron withdrawing groups at the meta position increase the cytotoxic potency, while substitution at the para position is not expected to increase the potency as compared to the parent taxane. Typically, a few representative taxanes with substituents at the different positions (ortho, meta and para) will be initially prepared and evaluated for in vitro cytotoxicity.

The thiol moiety can be introduced at one of the positions where a hydroxyl group already exists. The chemistry to protect the various hydroxyl groups, while reacting the desired one, has been described previously (see, for example, the references cited supra). The substituent is introduced by simply converting the free hydroxyl group to a disulfide-containing ether, a disulfide-containing ester, or a disulfide-containing carbamate. This transformation is achieved as follows. The desired hydroxyl group is deprotonated by treatment with the commercially-available reagent lithium hexamethyldisilazane (1.2 equivalents) in tetrahydrofuran at −40° C. as described in Ojima et al. (1999), supra. The resulting alkoxide anion is then reacted with an excess of a dihalo compound, such as dibromoethane, to give a halo ether. Displacement of the halogen with a thiol (by reaction with potassium thioacetate and treatment with mild base or hydroxylamine) will provide the desired thiol-containing taxane.

Alternatively, the desired hydroxyl group can be esterified directly by reaction with an acyl halide, such as 3-bromopropionyl chloride, to give a bromo ester. Displacement of the bromo group by treatment with potassium thioacetate and further processing as described above will provide the thiol-containing taxane ester.

CC-1065 Analogues

The cytotoxic agent according to the present invention may also be a CC-1065 analogue.

According to the present invention, the CC-1065 analogues contain an A subunit and a B or a B-C subunit. The A subunits are CPI (cyclopropapyrroloindole unit) in its natural closed cyclopropyl form or in its open chloromethyl form, or the closely related CBI unit (cyclopropylbenzindole unit) in the closed cyclopropyl form or the open chloromethyl form. The B and C subunits of CC-1065 analogues are very similar and are 2-carboxy-indole and a 2-carboxy-benzofuran derivatives. For activity, the analogues of CC-1065 need at least one such 2-carboxy-indole subunit or 2-carboxy-benzofuran subunit, although two subunits (i.e., B-C) render the analogue more potent. As is obvious from the natural CC-1065 and from the analogues published (e.g., Warpehoski et al, *J. Med. Chem.* 31:590–603 (1988)), the B and C subunits can also carry different substituents at different positions on the indole or benzofuran rings.

CC-1065 analogues containing a thiol moiety can be any of the following A subunits of the formulae A-1 {CPI (Cyclopropyl form)}, A-2 {CPI (Chloromethyl form)}, A-3 {CBI (Cyclopropyl form)}, and A-4 {CBI (Chloromethyl form)} covalently linked via an amide bond from the secondary amino group of the pyrrole moiety of the A subunit to the C-2 carboxy group of either a B subunit of the formula F-1 or a B-C subunit of the formulae F-3 or F-7.

A Subunits

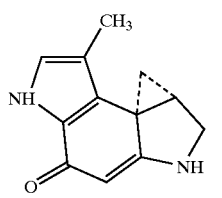
A-1

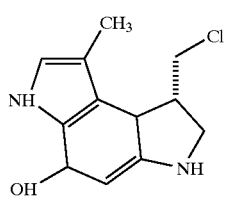
A-2

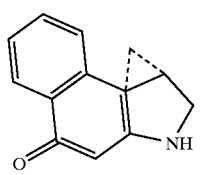
A-3

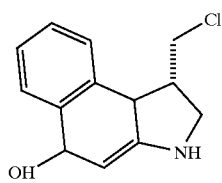
A-4

B and Covalently Bound B and C Subunits

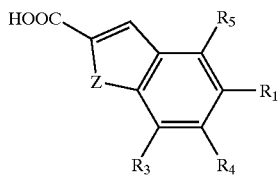
F-1

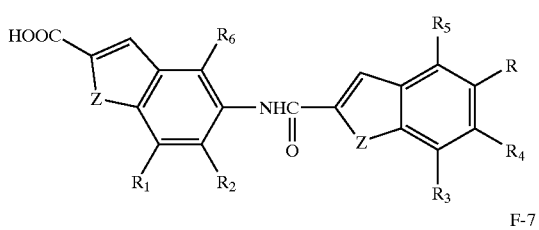
F-3

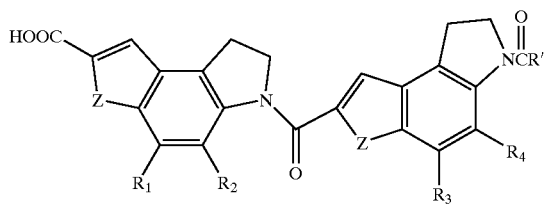
F-7 wherein each Z may be the same or different and may be O or NH; and wherein, in Formula F-1 $R_4$ is a thiol moiety, in Formula F-3 one of R or $R_4$ is a thiol moiety, in Formula F-7 one of R' or $R_4$ is a thiol-containing moiety; when R or R' is a thiol moiety, then $R_1$ to $R_6$, which may be the same or different, are hydrogen, $C_1$–$C_3$ linear alkyl, methoxy, hydroxyl, primary amino, secondary amino, tertiary amino, or amido; and when $R_4$ is a thiol moiety, R, $R_1$, $R_2$, $R_3$, $R_4$, $R_5$ and $R_6$, which may be the same or different, are hydrogen, $C_1$–$C_3$ linear alkyl, methoxy, hydroxyl, primary amino, secondary amino, tertiary amino, or amido, and R' is $NH_2$, alkyl, O-alkyl, primary amino, secondary amino, tertiary amino, or amido.

In a preferred embodiment, R and R' are thiol moieties and $R_1$ and $R_2$ are each hydrogen. In another preferred embodiment, R and R' are thiol moieties and $R_1$ to $R_6$ are each hydrogen.

In an especially preferred embodiment, R or $R_4$ is —NHCO(CH$_2$)$_l$SH, —NHCOC$_6$H$_4$(CH$_2$)$_l$SH, or —O(CH$_2$)$_l$SH, and R' is —(CH$_2$)$_l$SH, —NH(CH$_2$)$_l$SH or —O(CH$_2$)$_l$SH wherein l is an integer of 1 to 10.

Examples of primary amines include methyl amine, ethyl amine and isopropyl amine.

Examples of secondary amines include dimethyl amine, diethylamine and ethylpropyl amine.

Examples of tertiary amines include trimethyl amine, triethyl amine, and ethyl-isopropyl-methyl amine.

Examples of amido groups include N-methylacetamido, N-methyl-propionamido, N-acetamido, and N-propionamido.

Examples of alkyl represented by R', when R' is not a linking group, include $C_1$–$C_5$ linear or branched alkyl.

Examples of O-alkyl represented by R' when R' is not a linking group, include compounds where the alkyl moiety is a $C_1$–$C_5$ linear or branched alkyl.

The above-described CC-1065 analogues may be isolated from natural sources and methods for their preparation, involving subsequent modification, synthetic preparation, or a combination of both, are well-described (see, e.g., U.S. Pat. Nos. 5,475,092, 5,585,499 and 5,846,545).

Daunorubicin/Doxorubicin Analogues

The cytotoxic agent according to the present invention may also be a daunorubicin analogue or a doxorubicin analogue.

The daunorubicin and doxorubicin analogues of the present invention can be modified to comprise a thiol moiety.

The modified doxorubicin/daunorubicin analogues useful in the present invention have the formula D1 shown below:

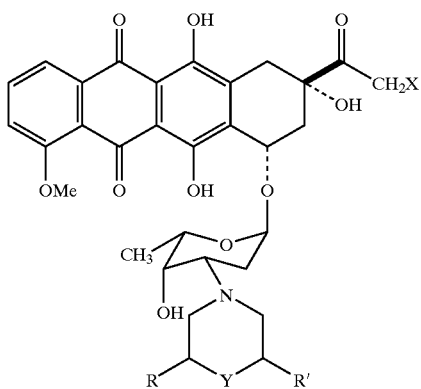

wherein,

X is H or OH;

Y is O or NR$_2$, wherein R$_2$ is linear or branched alkyl having 1 to 5 carbon atoms;

R is a thiol moiety, H, or liner or branched alkyl having 1 to 5 carbon atoms; and R' is a thiol moiety, H, or —OR$_1$, wherein R$_1$ is linear or branched alkyl having 1 to 5 carbon atoms;

provided that R and R' are not thiol moieties at the same time.

In a preferred embodiment, NR$_2$ is NCH$_3$. In another preferred embodiment, R' is —O.

In an especially preferred embodiment, the thiol moiety is —(CH$_2$)$_n$SH, —O(CH$_2$)$_n$SH, —(CH$_2$)$_n$CH(CH$_3$)SH, —O(CH$_2$)$_n$CH(CH$_3$)SH, —(CH$_2$)$_n$C(CH$_3$)$_2$SH, or —O(CH$_2$)$_n$C(CH$_3$)$_2$SH, wherein n is an integer of 0 to 10.

Examples of the linear or branched alkyl having 1 to 5 carbon atoms, represented by R, R$_1$, and R$_2$, include methyl, ethyl, n-propyl, isopropyl, n-butyl, isobutyl, sec.-butyl, tert.-butyl, and pentyl, in any of its eight isomeric arrangements.

R$_1$ and R$_2$ preferably are methyl.

Examples of linear alkyls include methyl, ethyl, propyl, butyl, pentyl and hexyl.

Examples of branched alkyls include isopropyl, isobutyl, sec.-butyl, tert.-butyl, isopentyl and 1-ethyl-propyl.

When either R or R' is not a linking group, the substituent in that position can be varied until a compound of the desired toxicity is obtained. High toxicity is defined as having an IC$_{50}$ towards cultured cancer cells in the range of $1 \times 10^{-12}$ to $1 \times 10^{-9}$ M, upon a 72 hour exposure time. Representative examples of substituents are H, alkyl, and O-alkyl, as described above. One of ordinary skill in the art can determine the appropriate chemical moiety for R and R' using only routine experimentation.

For example, methyl and methoxy substituents are expected to increase the cytotoxic potency, while a hydrogen is not expected to increase the potency as compared to the parent daunorubicin analogues with substituents at the different positions will be initially prepared and evaluated for in vitro cytotoxicity.

The modified doxorubicin/daunorubicin analogues of the present invention, which have a thiol moiety are described in WO 01/38318. The modified doxorubicin/daunorubicin analogues can be synthesized according to known methods (see, e.g., U.S. Pat. No. 5,146,064).

Analogues and Derivatives

One skilled in the art of cytotoxic agents will readily understand that each of the cytotoxic agents described herein can be modified in such a manner that the resulting compound still retains the specificity and/or activity of the starting compound. The skilled artisan will also understand that many of these compounds can be used in place of the cytotoxic agents described herein. Thus, the cytotoxic agents of the present invention include analogues and derivatives of the compounds described herein.

EXAMPLES

The invention will now be described by reference to non-limiting examples. Unless otherwise specified, all percents and ratios are by volume.

Example 1

Synthesis of 4-(5-Nitro-2-pyridyldithio)-pentanoic acid (NitroPPA, 8a)

A 100 L 2-necked flask was equipped with a stir bar, an addition funnel and a thermometer. The flask was charged with 1,3-dibromobutane (6) (5.2 g, 24 mmol) and dimethyl sulfoxide (30 mL). The addition funnel was charged with a solution of sodium cyanide (1.16 g, 24 mmol) in 5 mL of deionized water. The flask contents were vigorously stirred as the sodium cyanide solution was added dropwise at a rate which did not allow the reaction temperature to exceed 65° C. After addition was complete the reaction was stirred overnight. The mixture was extracted with deionized water (30 mL) and a 1:1 solution of ethyl acetate:hexanes (55 mL). The organic layer was retained and the aqueous layer was extracted a second time with 40 mL of 1:1 ethyl acetate:hexanes. The organic layers were combined and washed sequentially with deionized water (25 mL) and saturated aqueous sodium chloride (25 mL). The solvent was removed from the organic layer by rotary evaporation under reduced pressure (~15 torr). The residue was taken up in 15 mL of reagent grade ethanol and transferred to a 100 mL flask. The residue was treated with a solution of thiourea (2.6 g, 34 mmol) in H$_2$O (21 mL). The flask was equipped with a reflux condenser and was heated in an oil bath with stirring to give a mild reflux. After 4 hours the oil bath was removed and the flask was allowed to cool to room temperature. A solution of aqueous 10 M sodium hydroxide (25 mL) was added and the mixture was heated with an oil bath to a mild reflux with stirring overnight. The oil bath was removed and the flask was allowed to cool to room temperature. The solution was transferred to a separatory funnel and washed with ethyl acetate (2×25 mL). The aqueous layer was transferred to a 100 mL flask and cooled in an ice/water bath. Ethyl acetate (40 mL) was added and the contents were rapidly stirred as concentrated HCl was added until the aqueous layer was approximately pH 2. The mixture was transferred to a separatory funnel and extracted. The organic layer was retained and the aqueous layer was extracted a second time with 45 mL of ethyl acetate. The organic layers containing crude product 7 were combined and concentrated by rotary evaporation at room temperature to approximately 20 mL.

A 250 mL flask containing a stir bar was charged with 2,2'-dithiobis-(5-nitropyridine) (14.5 g, 47 mmol), tetrahydrofuran (170 mL) and diisopropylethyl amine (12.6 mL, 72 mmol). The flask was equipped with an addition funnel containing the solution of thiol acid 7, which was added drop-wise over approximately 8 min. The reaction was stirred for an additional 1 hour. Solvent was removed by rotary evaporation and the residue was taken up in a minimum of ethyl acetate and purified by silica chromatography. The column was eluted using a step gradient, starting with hexanes:ethyl acetate (4:1), until all of the unreacted 2,2'dithiobis-(5-nitropyridine) was removed. The column was then eluted with 4:1 hexanes:ethyl acetate containing 2% acetic acid. Fractions containing 4-(5-nitro-2-pyridyldithio)pentanoic acid were combined and solvent was removed by rotary evaporation giving pure 8a (2.3 g, 35% overall yield). MS ($M^+$+Na) $^1$H NMR (CDCl$_3$) 9.26 (d, 1H, J=2.5 Hz), 8.39 (dd, 1H J=2.5, 8.9 Hz), 7.89 (d, 1H, J=8.9 Hz), 3.08 (m, 1H), 2.58 (m, 2H), 1.97(m, 2H), 1.36 (d, 3H, J=6.7 Hz).

Example 2

N-Succinimidyl 4-(5-nitro-2-pyridyldithio)-pentanoate (1, SNPP)

A 50 mL flask was charged with 4-(5-nitro-2-pyridyldithio) pentanoic acid (8a, 0.51 g, 1.9 mmol), N-hydroxysuccinimide (0.24 g, 2.1 mmol) and a mixture of 1:1 tetrahydrofuran:methylene chloride (35 mL). The contents were stirred vigorously as a solution of 0.41 g of 1-(3-dimethylaminopropyl)-3-ethylcarbodiimide hydrochloride (0.41 g, 2.1 mmol) in tetrahydrofuran (5 mL) was added. The reaction mixture was stirred at room temperature for 2 h. The solvent was then removed by rotary evaporation under vacuum. The residue was dissolved in a minimum volume of methylene chloride and purified by silica chromatography using a mobile phase of 1:1.5 (v/v) tetrahydrofurane:hexane containing 0.5% acetic acid. Fractions containing pure product were combined and solvent was removed by rotary evaporation under vacuum to give the desired compound 1. $^1$H NMR (CDCl$_3$) 9.26 (d, 1H, J=2.5 Hz), 8.38 (dd, 1H, J=2.5 & 8.9 Hz), 7.84 (d, 1H, J=8.9 Hz), 3.13 (m, 1H), 2.85 (m, 6H), 2.04 (m, 2H), 1.38 (d, 3H, J=6.7 Hz).

Example 3

N-Sulfosuccinimidyl 4-(5-nitro-2-pyridyldithio)-pentanoate (2, SSNPP)

A 10 mL flask was charged with 4-(5-nitro-2-pyridyldithio) pentanoic acid (8a, 0.11 g, 0.41 mmol), N-hydroxysulfosuccinimide (0.83 g, 0.38 mmol), dicyclohexylcarbodiimide (0.080 g, 0.39 mmol), and dimethylacetamide (1.5 mL). The reaction mixture was stirred overnight. The flask was then cooled in an ice bath for 2 hours, and the precipitated dicyclohexylurea was filtered off. Ethyl acetate (45 mL) was added to the filtrate, the resulting suspension was stirred for 2 min, and the precipitate was collected by filtration. The precipitate was dried overnight under vacuum at room temperature, which yielded 0.092 g of 2 (51% yield). MS 463.9 ($M^-$–$Na^+$). $^1$H NMR (6:1 CDCl$_3$:DMSO-d$_6$) 8.68 (d,1H, J=2.5 Hz), 7.93 (dd, 1H J=2.5, 8.9 Hz), 7.42 (d, 1H, J=8.9 Hz), 3.51 (dd, 1H, J=8.8,2.8), 2.6 (m, 5H), 1.46 (m, 2H), 0.82 (d, 3H, J=6.7 Hz).

Example 4

Synthesis of N-succinimidyl 4-(2-pyridyldithio) butanoate (SPDB, 3a)

A solution of γ-thiobutyrolactone (9) (3.0 g, 29.4 mmol) in tetrahydrofuran (30 mL) and deionized water (20 mL) was prepared in a 100 mL round bottom flask. A solution of 5 M sodium hydroxide (9.86 mL, 49.3 mmol) was added to the reaction flask; the reaction proceeded under an argon atmosphere, with stirring, at room temperature. After 3 h, the solvent was removed under vacuo. Ethyl acetate (25 mL) and deionized water (25 mL) were added to the resulting crude oil, and the resulting solution was transferred to a separatory funnel and extracted, saving the aqueous phase. The aqueous phase was acidified to pH 3 using concentrated hydrochloric acid and extracted with ethyl acetate (2×25 mL). The combined organic layers were washed with a saturated sodium chloride solution (10 mL) and dried over anhydrous sodium sulfate. The resulting organic phase containing the product 4-mercaptobutanoic acid 10 was used in the next step without further purification.

The solution of 10 was transferred to an addition funnel and added dropwise to a magnetically stirred solution of 2,2'-dipyridyl disulfide (9.0 g, 41 mmol) in 50 mL of ethyl alcohol containing 1 mL of acetic acid. After 3 h, the solvent was removed by rotary evaporation under vacuum then the residue was taken up in a minimum volume of ethyl acetate and purified by silica chromatography using a mobile phase of hexanes:ethyl acetate:acetic acid (2:1:0.02, v/v/v). Fractions containing pure product were combined and solvent was removed under vacuum to give 4-(2-pyridyldithio) butanoic acid (11a) (5.1 g, 70% yield). $^1$H NMR (CDCl$_3$): δ 2.00–2.09 (2H, m), 2.46–2.55 (2H, m), 2.74 (1H, t, J=7.0), 2.86 (1H, t, J=7.0) 7.62–7.71 (1H, m), 7.71–7.78 (1H, m), 8.48–8.51 (1H, m), 11.8 (1H, br s).

Compound 11a (1.10 g, 4.8 mmol) and N-hydroxysuccinimide (0.64 g, 5.5 mmol) were dissolved in dichloromethane (50 mL). The solution was magnetically stirred as 1-[3-(dimethylamino)propyl]-3 ethylcarbodiimide (1.05 g, 5.5 mmol) was added. After 2 h, ethyl acetate (150 mL) was added and the solution was transferred to a separatory funnel and washed consecutively with 0.5 M HCl (30 mL) and saturated sodium chloride (20 mL). The organic layer was dried over anhydrous sodium sulfate, and then the solvent was removed under vacuum. The residue was taken up in a minimum volume of ethyl acetate and was purified by silica chromatography using a mobile phase of hexanes:ethyl acetate:acetic acid (2.5:1:0.02, v/v/v). Fractions containing pure product were combined and solvent was removed to give N-succinimidyl 4-(2-pyridyldithio) butanoate (SPDB, 3a) (1.2 g, 76% yield). $^1$H NMR (CDCl$_3$): δ 2.12–2.19 (2H, m), 2.78–2.87 (6H, m), 2.91 (2H, t, J=7.0), 7.06–7.12 (1H, m), 7.62–7.71 (2H, m), 8.48 (1H, d, 4.4 Hz). MS ($M+Na^+$) Found: 348.8 Calculated: 349.4.

Example 5

Synthesis of N-sulfosuccinimidyl 4-(5-nitro-2-pyridyldithio)butanoate (SSNPB, 3c)

A solution of the mercapto-carboxylic acid 10 (8.0 mmol) in ethyl acetate (10 mL) was transferred to an addition funnel and added dropwise to a stirring solution of 2,2'-dithiobis(5-nitropyridine) (3.0 g, 9.7 mmol) in tetrahydrofuran (50 mL) and 4-methylmorpholine (2.5 mL). The reaction mixture was stirred for 1 h. The reaction mixture was transferred to a 250 mL separatory funnel and treated with a solution of iodine (1.6 g) in ethyl acetate (100 mL). The contents were shaken vigorously for 5 min., diluted with hexane (40 mL), and then extracted with saturated aqueous sodium bicarbonate (2×70 mL). The combined aqueous layer was acidified with 1 M HCl and extracted with ethyl acetate (80 mL). The ethyl acetate layer was separated and dried over sodium sulfate, and filtered. The solvent was evaporated under vacuum and the residue was purified by silica chromatography using a mobile phase consisting of ethyl acetate:hexanes : acetic acid (85:12:3, v/v/v). Fractions containing pure product were combined and solvent was removed under vacuum to give the product 4-(5-nitro-2-pyridyldithio)butanoic acid, 11b (61% yield). $^1$H NMR (CDCl$_3$): δ 1.87–1.93 (2H, m), 2.43–2.54 (2H,m), 2.82–2.92 (2H,m), 7.89–7.92 (1H,m), 8.34–8.43 (1H,m), 9.23 (1H, s).

HPLC analysis using a Hewlett Packard reverse phase C18 (100×4.6 mm), eluting with a linear gradient of acetonitrile-H$_2$O (20% acetonitrile to 90% acetonitrile over 10 min) indicated that the product, which eluted with a retention time of 5.1 min, had a purity >98%.

A solution of 11b (200 mg, 0.73 mmol), sulfo-N-hydroxysuccinimide (180 mg, 0.81 mmol) and dicyclohexylcarbodiimide (175 mg, 0.85 mmol) in dimethylformamide (4.5 mL) was stirred over night at room temperature. Approximately ½ of the solvent was removed by rotary evaporation under vacuum and the resulting precipitate was removed by filtration. The filtrate was treated with 2-propanol (17 mL) that had been chilled to 4° C. The precipitate was collected by vacuum filtration and washed with ethyl ether (6 mL) at 4° C. Residual solvent was removed under vacuum to give 207 mg (60% yield) of product 3c. MS (M+Na$^+$) Found: 523.9 Calculated: 523.9, Neg Ion Found: 478.0 Calculated: 478.0.

Example 6

4-Mercapto-4-methylpentanoic acid (14)

A 500 mL flask was equipped with a stir bar and a 150 mL addition funnel. The system was placed under an argon atmosphere, and charged with anhydrous tetrahydrofuran (150 mL) and 2.5 M n-BuLi (75 mL, 18.7 mmol) in hexanes (18.7 mmol). The solution was cooled to −78° C. using a dry ice/acetone bath. Acetonitrile (7.3 g, 9.4 mL, 18 mmol) was added drop-wise via a syringe over approximately 5 min. The reaction was stirred for 30 min, while white lithium-acetonitrile precipitate was formed. Isobutylene sulfide (12), (15 g, 17 mmol) was dissolved in 100 mL of anhydrous THF and added dropwise over approximately 30 min via the addition funnel. The cooling bath was removed and the reaction was allowed to stir for 3 hours. The flask was cooled in an ice/water bath as of 0.5 M HCl (38 mL) was added drop-wise. The THF layer was retained and the aqueous layer was washed twice with 75 mL of ethyl acetate. The THF and ethyl acetate layers were combined, dried over approximately 20 g of anhydrous sodium sulfate and transferred to a 250 mL flask. Solvent was removed by rotary evaporation under vacuum to give crude 13. Ethanol (30 mL) was added, and the contents were stirred as a solution of NaOH (8.0 g) in deionized water (30 mL) was slowly added. The flask was equipped with a reflux condenser and placed under an argon atmosphere. The reaction was refluxed overnight and then cooled to room temperature. Deionized water (60 mL) was added and the mixture was washed with 2:1 (v/v) ethyl acetate:hexanes (2×25 mL). The aqueous layer was acidified to pH 2 with concentrated HCl, and then extracted with ethyl acetate (3×75 mL). The organic layers were dried over anhydrous sodium sulfate, filtered, and the solvent was removed by rotary evaporation under vacuum to give 10 g of product 14 (39% yield). The product was used without further purification. $^1$H NMR (CDCl$_3$): δ 1.38 (6H, s), 1.87–1.93 (2H, m), 2.08 (1H, s), 2.51–2.57 (2H, m).

Example 7

Synthesis of 4-methyl-4-(5-nitro-2-pyridyldithio)pentanoic acid (15a)

The concentrate containing 14 (18 mmol) was transferred to an addition funnel and added dropwise to a stirring solution of 2,2'-dithiobis(5-nitropyridine) (10.6 g, 34 mmol) in a mixture of tetrahydrofuran (50 mL), dimethyl formamide (150 mL) and 4-methylmorpholine (5.4 g, 53 mmol) The reaction mixture was stirred magnetically overnight. Solvent was evaporated under vacuum and the residue was taken up in 200 mL of ethyl acetate and vacuum filtered to remove material that did not dissolve. The filtrate was washed three times with 1 M HCl (3×50 mL) Solvent was removed under vacuum and then the residue was purified by silica chromatography using a mobile phase consisting of ethyl acetate:hexanes:acetic acid (85:12:3, v/v/v). Fractions containing pure product were pooled and solvent was removed by rotary evaporation under vacuum to give 4.1 grams of product 15a. $^1$H NMR (CDCl$_3$): δ1.38 (6H, s), 1.87–1.93 (2H, m), 2.59–2.63 (2H, m), 7.89–7.92 (1H, m), 8.34–8.43 (1H,m), 9.23 (1H, s).

Example 8

Synthesis of sulfo-N-succinimidyl-4-methyl-4-(5-nitro-2-pyridyldithio)pentanoate (4b)

A solution of 15a (0.25 g, 0.83 mmol), sulfo-N-hydroxysuccinimide (0.19 g, 0.86 mmol) and dicyclohexylcarbodiimide (0.19 g, 0.922 mmol) in dimethylformamide (5 mL) was stirred over night at room temperature. Approximately ½ of the solvent was removed by rotary evaporation under vacuum and the precipitate that formed was removed by filtration. The filtrate was treated with 2-propanol (20 mL that had been chilled to 4° C. The precipitate was collected by vacuum filtration and washed with ice-cold ethyl ether (15 mL). Residual solvent was removed under vacuum to give the desired product 4b (240 mg, 58% yield). MS (M+Na$^+$) Found: 496.0 Calculated 496.0. MS (M$^-$−Na$^+$): Found 450.1 Calculated. 450.0.

Example 9

Synthesis of 4-(5-N,N-dimethylcarboxamido-2-pyridyldithio)butanoic acid (17a)

A solution of 6-6'-dithiodinicotinic acid (16a) (1.6 g, 5.18 mmol) in dry dichloromethane (10 mL) and dimethyl formamide (4 mL) was prepared in a round bottom reaction flask and treated sequentially with 1-[3-(dimethylamino)propyl]-3-ethylcarbodiimide hydrochloride (EDC-HCl) (2.5 g, 12.9 mmol), dimethylamine (2.1 g, 26 mmol) and 4-methyl morpholine (1.63 g, 12.9 mmol). The reaction was allowed to proceed with stirring at room temperature for 2 h, after which time the reaction appeared complete upon analysis by analytical TLC, eluting in dichloromethane: methanol: acetic acid (93.9:6:0.1, v/v/v) which indicated that the starting material 16a had completely been converted to the dimethylamide derivative. The reaction mixture was treated with a mixture of 2:1 ethyl acetate/hexanes (15 mL) and washed sequentially using 50 mM potassium phosphate buffer, pH=6 (10 mL) and a saturated sodium chloride solution (5 mL). The organic phase was dried over anhydrous sodium sulfate. Evaporation of the solvent gave a crude residue. The product was purified by silica chromatography, eluting in a dichloromethane:methanol mixture (95:5 v/v respectively). The product containing fractions were combined; the solvent was removed in vacuo to give 16b as a yellow solid (35% yield). MS: m/z: Found: 385.0 (M+Na$^+$); Calculated: 385.0. $^1$H NMR (CDCl$_3$): δ 2.9 (6H, d, J=35), 7.6 (2H, dd, J=35 Hz and 10 Hz), 8.5 (1H, s).

A solution of 10 (0.54 g, 4.5 mmol) in ethyl acetate (11.5 mL) was added dropwise into a reaction flask containing 16b (2.6 g, 7 mmol) and 4-methyl morpholine (1.63 g, 16 mmol). The reaction was placed under an argon atmosphere, with stirring, at room temperature for 2 h, and the reaction volume was then concentrated by rotary evaporation to yield a crude yellow oil. The product was purified by silica chromatography, eluting in a 96:6:1 (dichloromethane:methanol:acetic acid, v/v respectively) mixture. The addition of toluene during rotary evaporation under high vacuum yielded the product 4-(5-N,N-dimethylcarboxamido-2-pyridyldithio)butanoic acid (17a) (76% yield). MS: m/z: Found 322.9 (M+Na$^+$); Calculated: 323.0.

Example 10

Synthesis of N-succinimidyl 4-(5-N,N-dimethylcarboxamido-2-pyridyldithio)butanoate (5a)

A solution of 17a (0.86 g, 2.86 mmol) in dichloromethane (30 mL) was prepared in a round bottom reaction flask and treated sequentially with 1-[3-(dimethylamino)propyl]-3-ethylcarbodiimide hydrochloride (0.82 g, 4.3 mmol) and N-hydroxy succinimide (0.49 g, 4.3 mmol). The reaction proceeded under an argon atmosphere, with stirring, at room temperature for two hours. Analysis by analytical TLC eluting in a dichloromethane:methanol:acetic acid mixture (93.9:6:0.1, v/v/v) showed that 17a had been fully converted to the succinimide ester 5a. Ethyl acetate (40 mL) was added to the reaction mixture, the combined organic phases were washed using pH=6, 50 mM potassium phosphate buffer (2×30 mL) and once using a saturated sodium chloride solution (15 mL). The resulting organic phase was dried over anhydrous sodium sulfate and the volume was reduced in vacuo. A portion of the crude material was purified by preparatory TLC, eluting in a dichloromethane:methanol:acetic acide mixture (93:6:1, v/v/v). The desired product was extracted from the silica using a 90:10 (dichloromethane:methanol) mixture to yield the purified modifying agent 5a (14% yield). MS: m/z: Found 420.0 (M+Na$^+$); Calculated: 420.0

HPLC analysis: Purity was determined by HPLC analysis using a Vydac analytical C-18 column (length: 100 mm, i.d.: 4.6 mm, particle size: 3 microns) at a flow rate of 1.5 mL/min eluting in a linear gradient of water and acetonitrile as follows:

| Time (min) | % Water | % Acetonitrile |
| --- | --- | --- |
| 0 | 80 | 20 |
| 20 | 50 | 50 |
| 25 | 0 | 100 |

Under these conditions, 5a eluted with a retention time of 7.68 min and the purity was 94.9%.

Example 11

Synthesis of sulfo-N-succinimidyl 4-(5-N,N-dimethylcarboxamido-2-pyridyldithio)butanoate (5b)

A solution of 17a (0.86 g, 2.86 mmol) in glass distilled dimethylformamide (30 mL) was prepared in a round bottom reaction flask and treated with sulfo-N-hydroxysuccinimide (0.63 g, 2.9 mmol). A solution of 1,3-dicyclohexylcarbodiimide (0.65 g, 3.2 mmol) in glass distilled dimethylformamide (10 mL) was prepared and added to the reaction flask. The reaction proceeded under an argon atmosphere, with stirring, at room temperature overnight. The resultant brown reaction mixture was filtered using coarse filter paper under vacuum; the filter cake was washed once using glass distilled dimethyl formamide (5 mL). The sulfo-succinimide ester 5b was precipitated using nine volumes of isopropanol, added slowly with stirring. The resultant precipitate was filtered and transferred to a pre-tarred vial to yield 5b as a white powder (47% yield). MS m/z: found 521.9 (M+Na$^+$); Calculated: 522.

HPLC analysis: Purity was determined by HPLC analysis using a Vydac analytical C-18 column (length: 100 mm, i.d.: 4.6 mm, particle size: 3 microns) at a flow rate of 1.5 mL/min eluting in a linear gradient of water and acetonitrile, going from 20% acetonitrile to 50% acetonitrile over 20 min. Under these conditions, 5b eluted with a retention time of 7.48 min and the purity was >90%.

Example 12

Conjugate Synthesis

SPP or SSNPP linker was dissolved in ethanol at a concentration of approximately 10 mM. Antibody was dialyzed into buffer A (50 mM KPi, 50 mM NaCl, 2 mM EDTA, pH 6.5). For the linker reaction, the antibody was at 8 mg/ml, and 7 equivalents of linker were added while stirring in the presence of 5% (v/v) ethanol. The reaction was allowed to proceed at ambient temperature for 90 minutes. Unreacted linker was removed from the antibody by Sephadex G25 gel filtration using a Sephadex G25 column equilibrated with Buffer A at pH 6.5 or 150 mM potassium phosphate buffer containing 100 mM NaCl, pH 7.4 as indicated. For the SPP linker, the extent of modification was assessed by release of pyridine-2-thione using 50 mM DTT and measuring the absorbance at 343 nm as described below ($\epsilon_{343}$=8080 $M^{-1}$ $cm^{-1}$ for free pyridine-2-thione). For SSNPP, modification was assessed directly by measuring the absorbance at 325 nm ($\epsilon_{325}$=10,964 $M^{-1}$ $cm^{-1}$ for the 4-nitropyridyl-2-dithio group linked to antibody). For the conjugation reaction, thiol-containing drug (either DM1 or DC4) was dissolved in DMA (N,N-dimethylacetamide) at a concentration of approximately 10 mM. The drug (0.8–1.7-fold molar excess relative to the number of linker molecules per antibody as indicated) was slowly added with stirring to the antibody which was at a concentration of 2.5 mg/ml in buffer A (pH 6.5 or pH 7.4) in a final concentration of 3% (v/v) DMA. The reaction was allowed to proceed at ambient temperature for the indicated times. Drug-conjugated antibody was purified using a Sephadex G25 column equilibrated with buffer B (PBS, pH 6.5). For DM1, the extent of drug conjugation to antibody was assessed by measuring $A_{252}$ and $A_{280}$ of the conjugate as described below. A similar approach was used for DC4 (see below).

Measurement of Releasable Pyridine-2-thione and Ab Concentration of SPP-Modified Ab. The molar ratio of pyridine-2-thione released per mole of antibody is calculated by measuring the $A_{280}$ of the sample and then the increase in the $A_{343}$ of the sample after adding DTT (50 µL of 1 M DTT/mL of sample). The concentration of DTT-released pyridine-2-thione is calculated using an $\epsilon_{343}$ of 8080 $M^{-1}cm^{-1}$. The concentration of antibody can then be calculated using an $\epsilon_{280}$ of 194,712 $M^{-1}cm^{-1}$ after subtracting the contribution of pyridine-2-thione absorbance at 280 nm ($A_{343\ nm}$ post DTT×5100/8080) from the total $A_{280}$ measured before DTT addition. The molar ratio of pyridine-2-thione:Ab can then be calculated. The mg/mL (g/L) concentration of Ab is calculated using a molecular weight of 147,000 g/mole.

Measurement of antibody-linked 5-Nitropyridyl-2-dithio Groups and Ab Concentration of SSNPP-Modified Ab. The molar ratio of the 4-nitropyridyl-2-dithio groups linked per mole of antibody is calculated by measuring the $A_{280}$ and $A_{325}$ of the sample without DTF treatment. The number of antibody-bound 4-nitropyridyl-2-dithio groups is calculated using an $\epsilon_{325\ nm}$ of 10,964 $M^{-1}cm^{-1}$. The concentration of antibody can then be calculated using an $\epsilon_{280}$ nm of 194,712 $M^{-1}cm^{-1}$ after subtracting the contribution of the 5-nitropyridyl-2-dithio group absorbance at 280 nm ($A_{325\ nm}$×3344/10964) from the total $A_{280\ nm}$ measured. The molar ratio of 4-nitropyridyl-2-dithio groups:Ab can then be calculated. The mg/mL (g/L) concentration of Ab is calculated using a molecular weight of 147,000 g/mole.

Calculating Ab and DM1 component concentrations of Ab-DM1. The Ab and DM1 both absorb at the two wavelengths used to measure each component separately, i.e., 280 and 252 nm. The components are quantified using the following algebraic expressions which account for the contribution of each component at each wavelength ($C_{Ab}$ is the molar concentration of Ab and $C_D$ is the molar concentration of DM1):

1) Total $A_{280}$=194712$C_{Ab}$+5,700$C_D$
2) Total $A_{252}$=(194,712×0.37)$C_{Ab}$+(4.7×5,700)$C_D$ Each equation is solved for $C_{Ab}$:

$$C_{Ab} = \frac{A_{280} - 5{,}700 C_D}{194{,}712} \quad \text{1a)}$$

$$C_{Ab} = \frac{A_{252} - 26{,}790 C_D}{72{,}043} \quad \text{2a)}$$

and an equality is set up (equation 1a=equation 2a) and solved for $C_D$:

$$C_D = \frac{A_{252} - 0.37 A_{280}}{24{,}681}$$

Once the $C_D$ is calculated, the value is used to solve for $C_{Ab}$ in equation 1a (or 2a) above. The ratio of DM1:Ab can then be calculated. The mg/mL (g/L) concentration of antibody is calculated using a molecular weight of 147,000 g/mole and the concentration of DM1 is calculated using a molecular weight of 736.5 g/mole (linked DM1)

Efficiency of disulfide exchange is increased with SSNPP. As shown in Table 1, the efficiency of conjugation is enhanced in reactions where SSNPP is used as the cross-linker compared to reactions using SPP. The percent efficiency was calculated by dividing the value for DM1 per antibody by the linker per antibody ratio times 100. Conjugations of the N901 antibody using SSNPP resulted in cross-linking efficiencies of 93% at both pH 6.5 and 7.4. The efficiency of conjugation of N901 with SPP in these experiments was 70% at pH 6.5 and 77% at pH 7.4. The increased efficiency with SSNPP demonstrates that a target DM1 to antibody ratio can be achieved using antibody that is modified with a reduced number of linker molecules. In fact, a similar drug to antibody ratio (4.3) was achieved in the final conjugate with an antibody preparation having 4.2 (5-nitropyridyl-2-dithio)-groups per antibody introduced with SSNPP compared to an antibody having 5.6 pyridyl-2-dithio groups introduced with SPP (Table 2). The amount of drug required to obtain comparable conjugation results was therefore 25% lower for the SSNPP-modified antibody than the SPP-modified antibody under these conditions. An additional potential benefit of the increased efficiency with SSNPP is that a reduced molar excess of DM1 may be used in the conjugation reaction. A comparison of the DM1 per antibody ratios following conjugation with a range of drug equivalents in the reaction (0.8–1.7 fold excess) shows that a 1.1-fold molar excess is sufficient to achieve 100% conjugation efficiency using the SSNPP cross-linker (FIG. 7). A comparison of the time course of the reaction of DM1 with antibody that had been modified with SSNPP or SPP is shown in FIG. 8. In each case the modified antibody was treated with a 1.1-fold molar excess of DM1 per mole of linker incorporated. The reaction with the SSNPP-modified antibody is considerably faster than with the SPP-modified antibody (FIG. 8). Even, a molar excess of 1.7-fold is not sufficient to achieve a similar efficiency using SPP. The ability to use 1) a lower molar excess of DM1 and 2) fewer linkers per antibody allows a reduction in the amount of drug needed to achieve a target DM1 to antibody ratio by as much as 50% when using SSNPP as the cross-linker instead of SPP.

The increased efficiency of conjugation using the SSNPP linker is accomplished without compromise in the monomeric character of the conjugate and in the amount of unconjugated (free) drug associated with the antibody conjugate. SEC analysis is used to determine the amount of monomer, dimer, trimer, or higher molecular weight aggregates. Typical results of greater than 90% monomer were obtained with either linker as shown in Table 1. The level of unconjugated drug was measured by reverse phase HPLC analysis of the conjugate sample. The percent free drug for either reaction was less than 2%. In addition, shorter conjugation reaction times are possible with SSNPP compared with SPP (5), which may decrease loss of some antibodies that are sensitive to prolonged exposure to organic solvent required in the conjugation reaction. Shorter reaction times should also decrease drug loss due to DM1 dimerization, which is a competing side reaction during conjugation. The resulting increases in yield and reduced side reactions should further contribute to reduced DM1 requirements.

The enhanced rate and efficiency of conjugation when using SSNPP was also observed when conjugating a different drug to the antibody demonstrating the broad applicability of this new linker reagent. A comparison of conjugation efficiencies using SSNPP and SPP when conjugating the N901 antibody with the DNA-alkylating drug, DC4, a CC-1065 analogue, is shown in Table 3. By 2 hours the reaction using the SSNPP cross-linking reagent was complete whereas the reaction using the SPP reagent showed only 73% completeness by 2 hours and significant incorporation of drug beyond 2 hours (91% after 18 hours). Only much prolonged reaction times may lead to 100% completeness.

TABLE 1

Comparison of SSNPP and SPP linker in the conjugation of N901 antibody with DM1. Conjugation was conducted for 2 hours at the indicated pH using a 1.7-fold molar excess of DM1 per linker.

| Linker | pH | Linker/Ab | DM1/Ab | % Efficiency | % free drug | SEC Analysis | | |
|---|---|---|---|---|---|---|---|---|
| | | | | | | Monomer | Dimer | Trimer | HMW |
| SSNPP | 7.4 | 4.1 | 3.8 | 93 | 0.8 | 91.9 | 6.3 | 0.6 | 0.1 |
| SPP | 7.4 | 5.6 | 4.3 | 77 | 1.8 | 93.6 | 4.9 | 0.4 | 0.2 |
| SSNPP | 6.5 | 4.0 | 3.7 | 93 | 0.9 | — | — | — | — |
| SPP | 6.5 | 6.6 | 4.6 | 70 | 1.9 | — | — | — | — |

TABLE 2

Reduced linker to antibody ratio required to reach target DM1 to antibody ratio with SSNPP as linker. Conjugation was conducted for 2 hours at pH 7.4 using a 1.1-fold molar excess of DM1 per linker.

| Linker | Linker/Ab | DM1/Ab |
|---|---|---|
| SSNPP | 4.2 | 4.3 |
| SPP | 5.6 | 4.3 |

TABLE 3

Comparison of SSNPP and SPP linker in the conjugation of N901 antibody with DC4. Conjugation was conducted for the indicated time at pH 7.4 using a 1.4-fold molar excess of DC4 per linker.

| Linker | Time, h | Linker/Ab | DC4/Ab | % efficiency |
|---|---|---|---|---|
| SSNPP | 2 | 4.2 | 4.3 | 102 |
| SSNPP | 18 | 4.2 | 4.1 | 98 |
| SPP | 2 | 5.6 | 4.1 | 73 |
| SPP | 18 | 5.6 | 5.1 | 91 |

What is claimed is:

1. A method of making a conjugate comprising a cell binding agent and one or more small molecule drugs, wherein said conjugate is represented by formula (V):

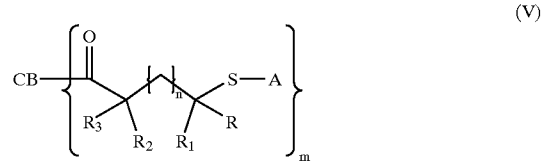

(V)

wherein CB represents the cell binding agent, A represents the small molecule drug linked by a disulfide moiety, R, $R_1$, $R_2$ and $R_3$ are the same or different and are H, methyl, ethyl, or linear, branched or cyclic alkyl having 3 to 6 carbon atoms, n is 0 or an integer from 1 to 4, and m is an integer of 1 to 10 or more, said method comprising:

(1) reacting the cell binding agent with a cross-linker of the formula (I):

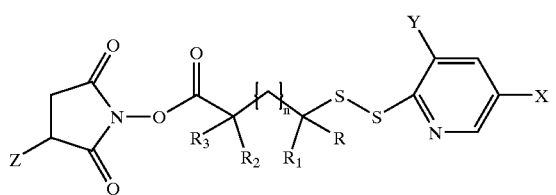

(I)

wherein X and Y are the same or different and are H, CONR$_4$R$_5$ or NO$_2$, provided that X and Y are not both H at the same time, R$_4$ and R$_5$ are the same or different and are each H, methyl, ethyl, n-propyl, isopropyl, n-butyl, sec-butyl, iso-butyl or tert-butyl, and Z is SO$_3^-$M$^+$ or H, wherein M$^+$ represents a metal ion or a tetra alkyl ammonium ion, to thereby give a compound of the formula (III):

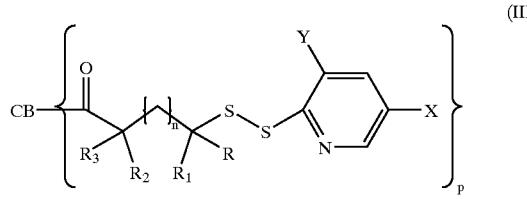

(III)

wherein p represents an integer of 1 to 10 or more, and (2) reacting the compound of the formula (III) with one or more small molecule drugs comprising a free thiol group.

2. A method of making a conjugate comprising a cell binding agent and one or more small molecule drugs, wherein said conjugate is represented by formula (V):

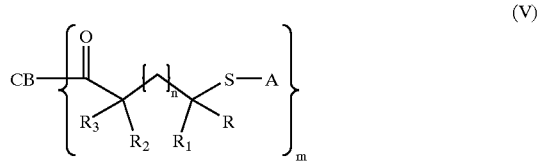

(V)

wherein CB represents the cell binding agent, A represents the small molecule drug linked by a disulfide moiety, R, R$_1$, R$_2$ and R$_3$ are the same or different and are H, methyl, ethyl, or linear, branched or cyclic alkyl having 3 to 6 carbon atoms, n is 0 or an integer from 1 to 4, and m is an integer of 1 to 10 or more, said method comprising:

(1) reacting the cell binding agent with a cross-linker of the formula (II):

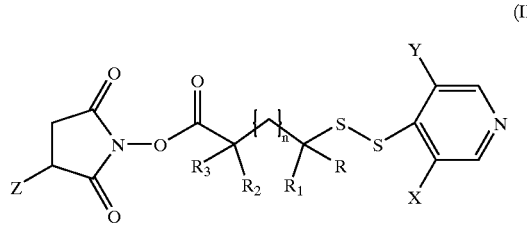

(II)

wherein X and Y are the same or different and are H, CONR$_4$R$_5$ or NO$_2$, provided that X and Y are not both H at the same time, R$_4$ and R$_5$ are the same or different and are each H, methyl, ethyl, n-propyl, isopropyl, n-butyl, sec-butyl, iso-butyl or tert-butyl, and Z is SO$_3^-$M$^+$ or H, wherein M$^+$ represents a metal ion or a tetra alkyl ammonium ion, to thereby give a compound of the formula (IV):

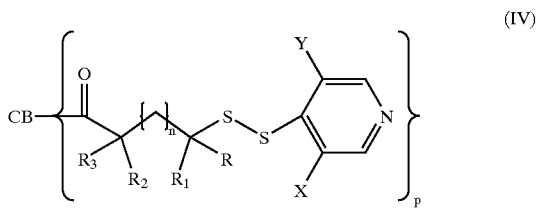

(IV)

wherein p represents an integer of 1 to 10 or more, and (2) reacting the compound of the formula (IV) with one or more small molecule drugs comprising a free thiol group.

3. The method of claim 1 or 2, wherein the cell-binding agent is an antibody or an antigen binding fragment thereof.

4. The method of claim 1 or 2, wherein the cell-binding agent is a monoclonal antibody or an antigen binding fragment thereof.

5. The method of claim 1 or 2, wherein the small molecule drug is a cytotoxic agent.

6. The method of claim 1 or 2, wherein the small molecule drug is at least one member selected from the group consisting of a maytansinoid compound, a taxane compound, a CC-1065 compound, a daunorubicin compound, a doxorubicin compound, and analogues or derivatives thereof.

7. The method of claim 1 or 2, wherein both of R and R$_1$ are H or methyl, or one of R and R$_1$ is H and the other is methyl.

8. The method of claim 1 or 2, wherein n is 1, R$_1$ is methyl, and R, R$_2$ and R$_3$ are H.

9. The method of claim 1 or 2, wherein n is 1 and R, R$_1$, R$_2$, and R$_3$ are H.

10. The method of claim 1 or 2, wherein n is 1, R and R$_1$ are both methyl, and R$_2$ and R$_3$ are both H.

11. A method of making a conjugate comprising a cell binding agent and one or more small molecule drugs, wherein said conjugate is represented by formula (V):

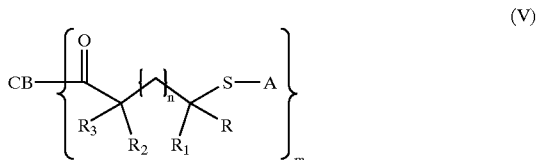

(V)

wherein CB represents the cell binding agent, A represents the small molecule drug linked by a disulfide moiety, R, R$_1$, R$_2$ and R$_3$ are the same or different and are H, methyl, ethyl, or linear, branched or cyclic alkyl having 3 to 6 carbon atoms, n is 0 or an integer from 1 to 4, and m is an integer of 1 to 10 or more, said method comprising:

reacting a compound of the formula (III)

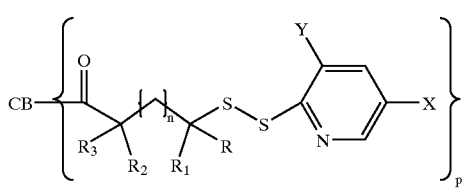

(III)

wherein X and Y are the same or different and are H, CONR$_4$R$_5$ or NO$_2$, provided that X and Y are not both H at the same time, R$_4$ and R$_5$ are the same or different and are each H, methyl, ethyl, n-propyl, isopropyl, n-butyl, sec-butyl, iso-butyl or tert-butyl, and p represents an integer of 1 to 10 or more, with one or more small molecule drugs comprising a free thiol group.

12. A method of making a conjugate comprising a cell binding agent and one or more small molecule drugs, wherein said conjugate is represented by formula (V):

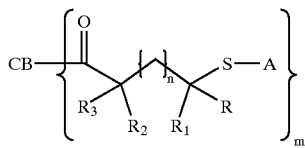

(V)

wherein CB represents the cell binding agent, A represents the small molecule drug linked by a disulfide moiety, R, R$_1$, R$_2$ and R$_3$ are the same or different and are H, methyl, ethyl, or linear, branched or cyclic alkyl having 3 to 6 carbon atoms, n is 0 or an integer of 1–4, and m is an integer of 1 to 10 or more, said method comprising:

reacting a compound of the formula (IV):

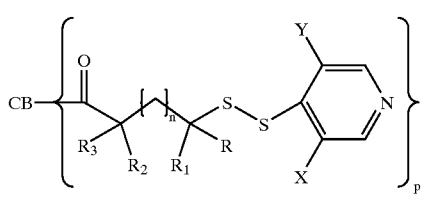

(IV)

wherein X and Y are the same or different and are H, CONR$_4$R$_5$ or NO$_2$, provided that X and Y are not both H at the same time, R$_4$ and R$_5$ are the same or different and are each H, methyl, ethyl, n-propyl, isopropyl, n-butyl, sec-butyl, iso-butyl or tert-butyl, and p represents an integer of 1 to 10 or more, with one or more small molecule drugs comprising a free thiol group.

13. The method of claim 11 or 12, wherein the cell-binding agent is an antibody or an antigen binding fragment thereof.

14. The method of claim 11 or 12, wherein the cell-binding agent is a monoclonal antibody or an antigen binding fragment thereof.

15. The method of claim 11 or 12, wherein the small molecule drug is a cytotoxic agent.

16. The method of claim 11 or 12, wherein the small molecule drug is at least one member selected from the group consisting of a maytansinoid compound, a taxane compound, a CC-1065 compound, a daunorubicin compound, a doxorubicin compound, and analogues or derivatives thereof.

17. The method of claim 11 or 12, both of R and R$_1$ are H or methyl, or one of R and R$_1$ is H and the other is methyl.

18. The method of claim 11 or 12, wherein n is 1, R$_1$ is methyl, and R, R$_2$ and R$_3$ are H.

19. The method of claim 11 or 12, wherein n is 1 and R, R$_1$, R$_2$, and R$_3$ are H.

20. The method of claim 11 or 12, wherein n is 1, R and R$_1$ are both methyl, and R$_2$ and R$_3$ are both H.

21. A cross-linker of formula (I):

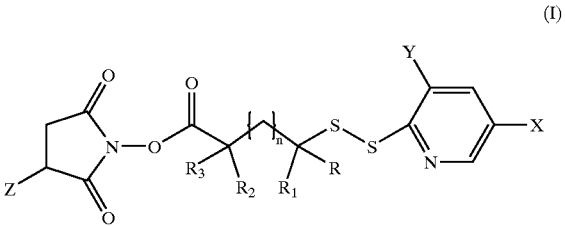

(I)

wherein R, R$_1$, R$_2$ and R$_3$ are the same or different and are H, methyl, ethyl, or linear, branched or cyclic alkyl having 3 to 6 carbon atoms, n is 0 or an integer from 1 to 4, X an Y are the same or different and are H, CONR$_4$R$_5$ or NO$_2$, provided that X and Y are not both H at the same time, R$_4$ and R$_5$ are the same or different and are each H, methyl, ethyl, n-propyl, isopropyl, n-butyl, sec-butyl, iso-butyl or tert-butyl, an Z is SO$_3^{31}$ M$^+$ or H, wherein M$^{31}$ represents a metal ion or a tetra alkyl ammonium ion, provided that when X and/or Y is NO$_2$, Z is not H.

22. A cross-linker of formula (II):

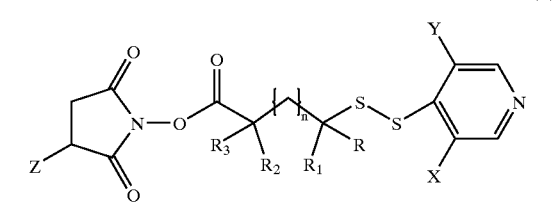

(II)

wherein R, R$_1$, R$_2$ and R$_3$ are the same or different and are H, methyl, ethyl, or linear, branched or cyclic alkyl having 3 to 6 carbon atoms, n is 0 or an integer from 1 to 4, X an Y are the same or different and are H, CONR$_4$R$_5$ or NO$_2$, provided that X and Y are not both H at the same time, R$_4$ and R$_5$ are the same or different and are each H, methyl, ethyl, n-propyl, isopropyl, n-butyl, sec-butyl, iso-butyl or tert-butyl, an Z is SO$_3^{31}$ M$^+$ or H, wherein M$^{30}$ represents a metal ion or a tetra alkyl ammonium ion, provided t at when X and/or Y is NO$_2$, Z is not H.

23. The cross-linker of claim 21 or 22, wherein both of R and R$_1$ are H or methyl, or one of R and R$_1$ is H and the other is methyl.

24. The cross-linker of claim 21 or 22, wherein n is 1, R$_1$ is methyl and R, R$_2$ and R$_3$ are H.

25. The cross-linker of claim 21 or 22, wherein n is 1 and R, R$_1$, R$_2$, and R$_3$ are H.

26. The cross-linker of claim 21 or 22, wherein n is 1, R and $R_1$ are both methyl, and $R_2$ and $R_3$ are both H.

27. A method of making a compound of formula (III):

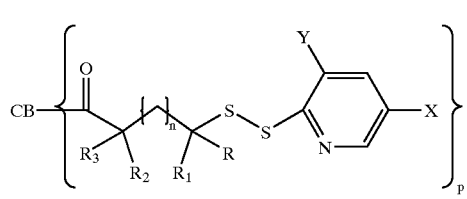

(III)

wherein CB represents a cell binding agent, R, $R_1$, $R_2$ and $R_3$ are the same or different and are H, methyl, ethyl, or linear, branched or cyclic alkyl having 3 to 6 carbon atoms, n is 0 or an integer from 1 to 4, X and Y are the same or different and are H, $CONR_4R_5$ or $NO_2$, provided that X and Y are not both H at the same time, $R_4$ and $R_5$ are the same or different and are each H, methyl, ethyl, n-propyl, isopropyl, n-butyl, sec-butyl, iso-butyl or tert-butyl, and p represents an integer of 1 to 10 or more, comprising reacting the cell binding agent, CB, with a cross-linker of the formula (I):

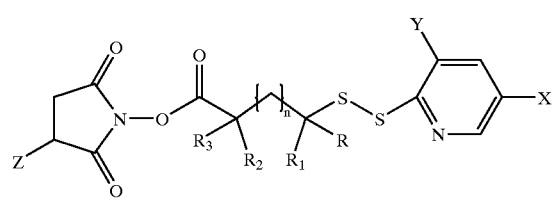

(I)

wherein Z is $SO_3^-M^H$, wherein $M^{30}$ represents a metal ion or a tetra alkyl ammonium ion.

28. A method of making a compound of formula (IV):

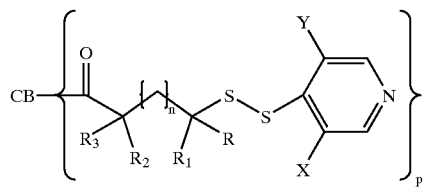

(IV)

wherein CB represents a cell binding agent, R, $R_1$, $R_2$ and $R_3$ are the same or different and are H, methyl, ethyl, or linear, branched or cyclic alkyl having 3 to 6 carbon atoms, n is 0 or an integer from 1 to 4, X and Y are the same or different and are H, $CONR_1R_5$ or $NO_2$, provided that X and Y are not both H at the same time, $R_4$ and $R_5$ are the same or different and are each H, methyl, ethyl, n-propyl, isopropyl, n-butyl, sec-butyl, iso-butyl or tert-butyl, and p represents an integer of 1 to 10 or more, comprising reacting the cell binding agent with a cross-linker of the formula (II):

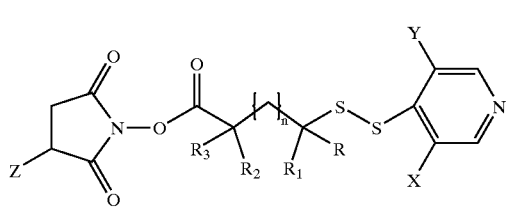

(II)

wherein Z is $SO_3^{31}$ $M^+$ or H, wherein $M^+$ represents a metal ion or a tetra alkyl ammonium ion.

29. The method of claim 27 or 28, wherein the cell-binding agent is an antibody or an antigen binding fragment thereof.

30. The method of claim 27 or 28, wherein the cell-binding agent is monocloanal antibody or an antigen binding fragment thereof.

31. the method of claim 27 or 28, wherein both of R and $R_1$ are H or ethyl, or one of R and $R_1$ is H and the other is methyl.

32. The method of claim 27 or 28, wherein n is 1, $R_1$ is methyl, and R, $R_2$ and $R_3$ are H.

33. The method of claim 27 or 28, wherein n is 1 and R, $R_1$, $R_2$, and $R_3$ are H.

34. The method of claim 27 or 28, wherein n is 1, R and $R_1$ are both methyl, and $R_2$ and $R_3$ are both H.

* * * * *